US008134459B2

(12) United States Patent
Smith et al.

(10) Patent No.: US 8,134,459 B2
(45) Date of Patent: *Mar. 13, 2012

(54) WIRELESS TELECOMMUNICATIONS SYSTEM ADAPTABLE FOR PATIENT MONITORING

(75) Inventors: Guy Smith, Waukesha, WI (US); Matthew T. Oswald, Wauwatosa, WI (US); Matthew L. Brown, Waukesha, WI (US); Matthew E. Ellis, Waukesha, WI (US)

(73) Assignee: Smiths Medical ASD, Inc., Rockland, MA (US)

( * ) Notice: Subject to any disclaimer, the term of this patent is extended or adjusted under 35 U.S.C. 154(b) by 866 days.

This patent is subject to a terminal disclaimer.

(21) Appl. No.: 11/907,983

(22) Filed: Oct. 19, 2007

(65) Prior Publication Data

US 2009/0105549 A1   Apr. 23, 2009

(51) Int. Cl.
G08B 1/08 (2006.01)
A61B 5/00 (2006.01)

(52) U.S. Cl. ............... 340/539.12; 600/301; 340/539.13

(58) Field of Classification Search .................. None
See application file for complete search history.

(56) References Cited

U.S. PATENT DOCUMENTS

| | | | |
|---|---|---|---|
| 5,839,439 A | 11/1998 | Nierlich et al. | |
| 5,944,659 A * | 8/1999 | Flach et al. | 600/300 |
| 6,470,893 B1 * | 10/2002 | Boesen | 128/899 |
| 6,589,170 B1 | 7/2003 | Flach et al. | |
| 6,694,180 B1 * | 2/2004 | Boesen | 600/547 |
| 6,705,990 B1 | 3/2004 | Gallant et al. | |
| 6,804,558 B2 | 10/2004 | Haller et al. | |
| 7,156,807 B2 * | 1/2007 | Carter et al. | 600/300 |
| 7,463,902 B2 * | 12/2008 | Boesen | 455/522 |
| 2002/0008625 A1 * | 1/2002 | Adams et al. | 340/573.1 |
| 2002/0069885 A1 | 6/2002 | Boies et al. | |
| 2003/0181798 A1 | 9/2003 | Al-Ali | |
| 2005/0197550 A1 | 9/2005 | Al-Ali et al. | |
| 2006/0007882 A1 | 1/2006 | Zeng et al. | |
| 2006/0056363 A1 | 3/2006 | Ratiu et al. | |
| 2006/0122469 A1 * | 6/2006 | Martel | 600/300 |
| 2006/0202816 A1 * | 9/2006 | Crump et al. | 340/539.12 |
| 2006/0276714 A1 * | 12/2006 | Holt et al. | 600/481 |
| 2007/0011028 A1 | 1/2007 | Sweeney | |
| 2007/0030116 A1 * | 2/2007 | Feher | 340/5.53 |
| 2007/0135866 A1 | 6/2007 | Baker et al. | |
| 2007/0180140 A1 | 8/2007 | Welch et al. | |

(Continued)

*Primary Examiner* — Sam Yao
*Assistant Examiner* — Shirley Jian
(74) *Attorney, Agent, or Firm* — Louis Woo

(57) ABSTRACT

A wireless network having an architecture that resembles a peer-to-peer network has two types of nodes, a first sender type node and a second receiver/relay type node. The network may be used in a medical instrumentation environment whereby the first type node may be wireless devices that could monitor physical parameters of a patient such as for example wireless oximeters. The second type node are mobile wireless communicators that are adapted to receive the data from the wireless devices if they are within the transmission range of the wireless devices. After an aggregation process involving the received data, each of the node communicators broadcasts or disseminates its most up to date data onto the network. Any other relay communicator node in the network that is within the broadcast range of a broadcasting communicator node would receive the up to date data. This makes it possible for communicators that are out of the transmitting range of a wireless device to be apprized of the condition of the patient being monitored by the wireless device. Each communicator in the network is capable of receiving and displaying data from a plurality of wireless devices.

23 Claims, 20 Drawing Sheets

Exemplar Wireless Data Flow

U.S. PATENT DOCUMENTS

| | | |
|---|---|---|
| 2007/0219059 A1* | 9/2007 | Schwartz et al. ............... 482/8 |
| 2007/0255250 A1 | 11/2007 | Moberg et al. |
| 2007/0258395 A1 | 11/2007 | Jollota et al. |
| 2007/0262863 A1* | 11/2007 | Aritsuka et al. ......... 340/539.22 |
| 2007/0273504 A1* | 11/2007 | Tran ........................ 340/539.12 |
| 2007/0276270 A1* | 11/2007 | Tran ............................... 600/508 |
| 2008/0001735 A1* | 1/2008 | Tran ........................ 340/539.22 |
| 2008/0004538 A1 | 1/2008 | Virtanen |
| 2008/0221420 A1 | 9/2008 | Grubac et al. |
| 2008/0272918 A1 | 11/2008 | Ingersoll |

* cited by examiner

Exemplar System Overview

Simple Overall Communicator Block Diagram

Communicator Block Diagram

Wireless Oximeter/Sensor Block Diagram

Communicator with a Wireless Oximeter/Sensor

Communicator with an Oximeter Sensor

Exemplar Wireless Data Flow

Time Slotted Scheduled Communications

FIG. 10
Message Types

| | Message | Size (bytes) | Flow | Constancy | Frequency |
|---|---|---|---|---|---|
| M6 | Wireless Sensor (WS) | 96 | Sensor X to CO X | Persistent | >=1 Hz |
| M5 | Remote Data Display (RDD) | 96 | Every CO broadcasts to all CO | Persistent | >=1 Hz |
| M4 | High Speed 1 (HS1) | 96 | Selectively sourced from any one CO, rebroadcast by all CO, displayed by any CO | On Demand | >=1 Hz |
| M3 | High Speed 1 (HS1) | 96 | Selectively sourced from any one CO, rebroadcast by all CO, displayed by any CO | On Demand | >=1 Hz |
| M2 | Control (CTR) | <=30 | CO X to/from Sensor X | Asynchronous | >=1 Hz |
| M1 | Network Control (NWK) | <=30 | Every CO broadcasts to all CO AND / OR CO X to/from Sensor X | May Vary | As required for network control |

Remote Data Display Messages - Aggregate and Flood

Wireless Sensor Power Draw

Communicator Block Diagram

Wireless Finger Oximeter/Sensor

Radio State Transition Diagram

Radio RF Receive Flowchart

Radio RF Transmit Flowchart

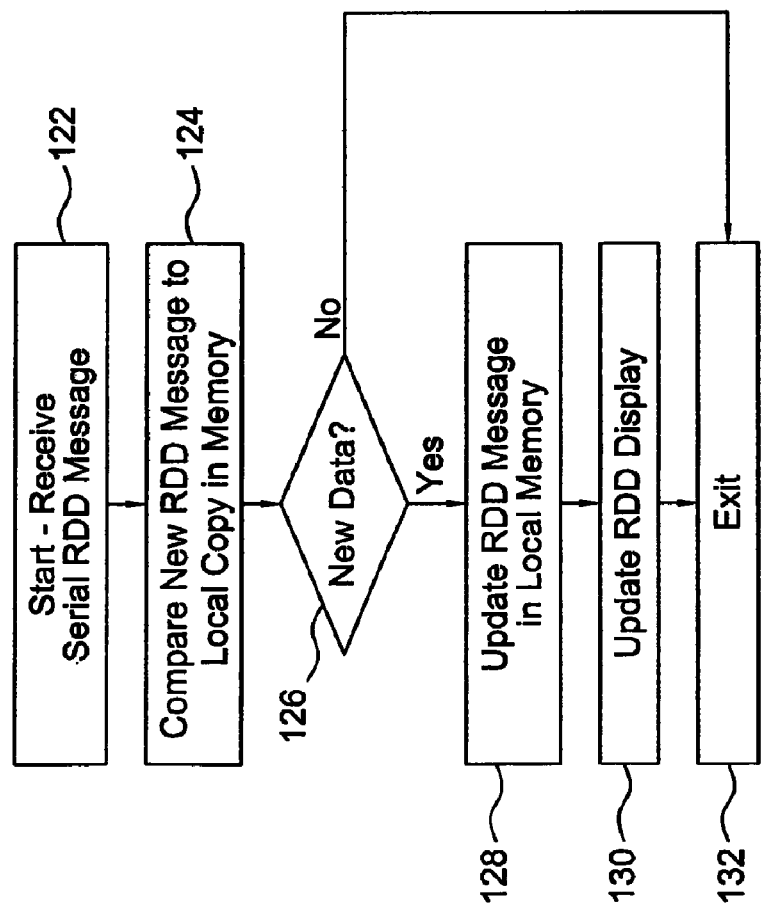

RDD Radio Flow Chart (Aggregate and Forward)

Wireless Finger Oximeter/Sensor Operational Flow Chart

WIRELESS TELECOMMUNICATIONS SYSTEM ADAPTABLE FOR PATIENT MONITORING

FIELD OF THE INVENTION

The present invention relates to a wireless telecommunications network that may be used in the medical industry, and more particularly relates to a nodal network that has a plurality of node communicators for conveying patient parameters remotely from the site where the patient is being monitored. Also disclosed are inventions that relate to the method of remotely conveying or propagating patient information along the network and the devices used in such wireless telecommunications network.

BACKGROUND OF THE INVENTION

To remotely monitor physical parameters, for example blood pressure, arterial oxygen blood saturation (SP02), heart rate, electrocardiogram, etc., of a patient, a sensor is usually attached to the patient, with the sensor being connected to a transmitter that transmits the patient signals to a central nursing station. Such transmission is usually by hardwire, and more recently wirelessly. At the nursing station, which may either be located in the general ward or in an intensive care unit (ICU) of a hospital, a number of monitors are provided to monitor the patients in the various rooms. There is always a nurse at the nursing station who monitors the physical parameters of the different patients that are being transmitted from the various patient rooms, in order to observe the physical well-being of the patients. Such central nursing station works well in an environment whereby the patients are confined to their respective rooms, with each of the rooms containing the appropriate transmitter for transmitting the physical parameters sensed by the sensor(s) connected to the respective patients.

There is however a trend in the medical field to incorporate wireless communications to provide mobility for the patient. In the medical field, for example in the area of pulse oximetry, one such portable device is a finger oximeter with remote telecommunications capabilities that is disclosed in U.S. Pat. No. 6,731,962, assigned to the assignee of the instant application. The disclosure of the '962 patent is incorporated by reference herein. The '962 device is adaptable to transmit patient data to a remote receiver or monitor. Another pulse oximeter that is capable of communicating with an external oximeter via a wireless communications link is disclosed in patent publication 2005/0234317. The remote device for this oximeter is a display. Another wireless pulse oximeter is disclosed in patent publication 2005/0113655. There a wireless patient sensor would transmit raw patient data to a pulse oximeter that processes the data and further configures the data to generate a web page, which is then transmitted wirelessly to a wireless access point, so that the web page may be downloaded by remote monitoring stations that are connected by means of a network to the access point. Another system that remotely monitors the conditions of a patient is disclosed in patent publication 2004/0102683. The '683 publication discloses a patient monitoring device worn by the patient. The patient data collected from the patient is transmitted wirelessly to a local hub. The hub then transfers the data to a remote server by way of a public or private communications network. The server is configured as a web portal so that the patient data may be selectively accessed by physicians or other designated party that are allowed to view the patient's data.

The current systems therefore are focused to the transmitting of patient data to a remote hub or access point and are therefore confined to a specific site from which the patient data may be reviewed remotely. The network or communications link that are currently used are thus either predefined links that transmit information in a particular communications path, or by means of public communications network with a particular server from which selective access may be granted. Yet all of these prior art system are not particularly suited to the above mentioned hospital environment in which there is a need to provide mobility for the patients, as well as the need to monitor the multiple patients. Moreover, there is a need to un-tether the patient from the monitor that is fixed to the room of the patient to provide the patient more mobility, and yet at the same time, allows the care-giver(s) to continue to monitor the physical well being of the patient.

There is therefore a need for a portable device that may be worn by a patient which can wirelessly transmit data collected from a patient.

Further, given the shortage of care-givers, there is a need to reduce the requirement for a particular nurse or care-giver to be stationed at for example a central nursing station, in order to monitor the physical parameters of the various patients. It may also be advantageous to have more than one care-giver who could monitor the different physical parameters of the various patients. It follows then that there is also a need to enable a nurse or care-giver, or a number of nurses or care-givers or other healthcare personnel, to be able to monitor remotely in substantially real time the physical well being of a patient, and/or the various patients in this communications network. To that end, There is a need for a communications network that could receive the data collected from the various patients, and at the same time correlate the different data collected with the various patients. To fully enable the remote monitoring capabilities of the network, a need therefore also arises for a portable device to be carried by each care-giver to thereby un-tether the care-giver(s) from any particular central monitoring location.

BRIEF SUMMARY OF THE PRESENT INVENTION

The present invention, among its multiple aspects which may themselves constitute self standing inventions, attempts to overcome the need for a central server or hub to which the data collected from the patient is routed, per taught by the prior art. The present invention therefore aims to, in the one aspect, provide remote monitoring across a network, for example a peer-to-peer network or a mesh network with a deterministic configuration, so that there is no reliance on a single hub or access point.

The present invention, in one aspect, more particularly relates to a wireless communications network that is adapted for use by medical devices and that has an architecture that may be in the form of a peer-to-peer network of medical devices without a network controller. Each of the medical devices may be considered a node of the network, with the medical devices or nodes being time synchronized and the communications among the devices scheduled, to thereby eliminate in network interference and allow good quality both in terms of the communications among the nodes and the types of messages disseminated among the devices.

In an embodiment of the instant invention set in an exemplar medical environment, for example oximetry, a patient whose physiological parameters or attributes are to be measured has attached to him or her a sensor module that has a sensor to measure the physical parameters of the patient. The obtained patient data may be routed by the sensor to a transmitter for transmission. Alternatively, the sensor module may in itself contain a transmitter for transmitting the measured physical parameters of the patient. A transceiver may also be provided in the sensor module in the event that bidirectional communications between the sensor module and a remote receiver is desired. The sensor module may be referred to, in the being discussed medical environment, as a wireless oximeter sensor. Each of the wireless oximeter sensor may include an oximeter and its associated sensor, as well as a transceiver or radio for outputting or transmitting the patient data obtained by the sensor.

The receiver that receives the signal output from the sensor attached to the patient may be a bi-directional communication device referred henceforth as a communicator that has a transceiver for receiving and transmitting information or data. At least one memory is provided in the communicator for storing the most up to date information that it has received. In addition to the transceiver and the memory, the communicator may also have a processor, an user interface, a power circuit and in the case of it communicating with an oximeter sensor, an oximeter circuit. The communicator is adapted to aggregate information received or collected, so that data from the communicator may be disseminated or broadcast out toward the network.

There may be a plurality of communicators in the communications network of the instant invention, with each communicator being considered a node of the network. As the network is comprised of a plurality of nodes each being a communicator, the communication of data through the network therefore is consistent and controllerless. Moreover, as each of the communicators is mobile, the topology of the network changes and therefore the network is topology independent and resembles a peer-to-peer architecture. The size the network depends on the number of communicators or nodes that are in the network. One exemplar network may comprise from a minimum of two communicators to a maximum of N communicators, or nodes. Each transceiver, or radio, in each of the communicators has a broadcast or transmission range of a predetermined distance, so that the information broadcast from one communicator would cover a given transceiving area. Other communicators or nodes within the network that are within the transmission range of another communicator would receive the data that is being broadcast from that other communicator. Conversely, that other communicator will receive data that is broadcast from the communicators that are within its own reception range. Thus, data may be communicated among the different communicators, or nodes, of the network. There is therefore no dedicated access point, coordinator or controller in the network of the instant invention.

Not all nodes in the network are communicators, as wireless oximeters, or other medical devices, that are meant to be attached to the patient for monitoring or measuring physical parameters of the patient may also be considered as nodes of the network. For the instant invention, such wireless oximeter, and other types of medical devices that are adapted to measure or sense physical attributes from a patient, may be considered as a sensor node of the network. Alternatively, sensor nodes that collect information from the patient and transmit the collected information to the network may also be referred to as first type nodes of the network. It follows then that the second type nodes for the network of the instant invention are the communicators that receive, aggregate and broadcast the data received from the patient via the first type nodes, i.e., the wireless oximeter sensors. The communications protocol for the different types of nodes, or among the wireless sensors and the communicators, may be based on the IEEE Standard 802.15.4.

So that the various nodes of the network can communicate with each other, the devices of the network are time synchronized and follow a given communications schedule. For synchronization, the nodes of the network each are assigned time slots, with each time slot divided into subslots. Each of the nodes, or devices, is synchronized by means of communications from its neighbor(s), so that each node transmits data only in the time slot allotted to it. The communication schedule is cyclic so that all nodes on the network are scheduled to transmit or broadcast their stored data, in accordance with the respective assigned slots for the different communicator devices that form the network.

As data is disseminated or propagated from one node to the other nodes, the data is aggregated in each of the nodes that received the data. The aggregated data is disseminated across the network, so that the messages being propagated across the network are continuously updated. Aggregation takes place in a node when the message received by that node is newer than the message previously stored in that node.

In a first aspect, the present invention is directed to a system for communicating information relating to physical attributes of a patient. The system includes at least one patient monitoring device associated with a patient that has a sensor for detecting at least one physical attribute of the patient, and at least one transmitter for transmitting patient data corresponding to the detected physical attribute out to a device transmission area. There is also included in the system a plurality of communicators each having a transceiver adapted to at least receive the data transmitted from the patient monitoring device when it is located within the device transmission area. Each of the communicators communicates with other communicators that are within its transceiving area. For the inventive system, any one of the communicators, when located within the device transmission area, is adapted to receive the patient data from the patient monitoring device, and after receipt of the patient data, broadcast the patient data to other communicators that are located within its communicator transceiving area.

Another aspect of the invention is directed to a system for communicating information relating to physical attributes of patients that includes multiple patient monitoring devices each associated with a particular patient. These patient monitoring devices each have sensor means for detecting at least one physical attribute of the patient associated with the device and a transmitter for transmitting the patient data that corresponds to the physical attribute to a transmission area of the device. There is also included in the inventive system a plurality of communicators each having a transceiver adapted to receive patient data transmitted from the patient monitoring devices when located within the respective transmission areas of the patient monitoring devices. Each of the communicators is adapted to communicate with the other communicators within its transceiving area. Each of the communicators, when located within the transmission area of any one of the patient monitoring devices, is therefore adapted to receive the patient data from the any one patient monitoring device and thereafter broadcast the received patient data out to its own communicator transceiving area.

A third aspect of the instant invention is directed to a system for disseminating information relating to physical attributes of a patient remotely that includes at least one oximeter associated with a patient having sensor means for detecting at least the SP02 of the patient. The oximeter includes at least a transmitter or transceiver to at least transmit patient data corresponding to the detected SP02 away from the device. The system further includes a plurality of communicators each having a transceiver adapted to receive the data transmitted from the patient oximeter when located within the transmission range of the patient oximeter. Each of the communicators is adapted to communicate with the other communicators, so that when one of the communicators is located within the transmission range of the oximeter, it would receive the patient data from the patient oximeter and thereafter broadcast the received patient data to the other communicators that are located within its broadcast range.

A fourth aspect of the instant invention is directed to a communications network where information relating to physical attributes of a patient may be conveyed remotely. The inventive communications network includes at least one wireless sensor associated with a patient for detecting at least one physical attribute of a patient. The sensor includes at least a transmitter for transmitting patient data corresponding to the detected physical attribute away from the sensor. The network further includes a first communicator located within transmission range of the sensor having a transceiver adapted to receive the patient data transmitted from the sensor and to broadcast the received patient data. The inventive communications network further includes a second communicator in communication with the first communicator but not in communication with the wireless sensor. The second communicator has a second transceiver adapted to receive the patient data broadcast by the first communicator.

A fifth aspect of the instant invention is directed to a wireless network having a plurality of nodes for disseminating information of patients. The inventive wireless network includes at least a first type node adapted to be associated with a patient for monitoring the physical attributes of the patient. The first type node includes a detector that detects at least one physical attribute of the patient and a transmitter that transmits the detected physical attribute of the patient as data out to the network. There may also be included in the network a plurality of mobile second type nodes not directly associated with the patient that are adapted to receive signals and/or data from the first type node when moved to within the broadcast range of the first type node. Each of the second type nodes further is adapted to receive the signals and/or data from other second type nodes and to broadcast signals and/or data onto the network. The wireless network of this aspect of the invention allows any one of the second type nodes, when moved to within the broadcast range of the first type node, to receive the patient data output from the first type node, and thereafter to broadcast the received patient data out to the network so that any other second type node located within the broadcast range of the one second type node would receive the patient data output from the first type node.

A sixth aspect of the invention is directed to a wireless network that has a plurality of nodes for disseminating information of patients. This inventive wireless network includes multiple first type nodes each adapted to be associated with a particular patient for monitoring the physical attributes of the particular patient. Each of the first type nodes includes a detector that detects at least one physical attribute of the particular patient and a transmitter that transmits the detected physical attribute as patient data out to the network. The wireless network further includes a plurality of mobile second type nodes not directly associated with any patient that are adapted to receive signals and/or data from the first type nodes when moved to within the broadcast range of any of the first type nodes. Each of the second type nodes further is adapted to receive signals and/or data from other second type nodes and to broadcast signals and/or data out onto the network. When one of the second type nodes is moved to within the broadcast range of any of the first type nodes, the one second type node would receive the patient data output from that first type node. The one second type node then would broadcast the receive patient data out to the network so that any other second type node located within the broadcast range of the one second type node would receive the patient data output by the first type node.

A seventh aspect of the instant invention is directed to a method of disseminating information relating to physical attributes of patients. The method includes the steps of: a) associating at least one patient monitoring device having sensor means and at least a transmitter with a patient; b) detecting at least one physical attribute from the patient using the sensor means; c) transmitting patient data corresponding to the one detected physical attribute out to a device transmission area; d) providing a plurality of communicators each having a transceiver adapted to receive data transmitted from the patient monitoring device and to broadcast data out to a communicator transceiver area; e) locating one of the plurality of communicators within the device transmission area of the one patient monitoring device to receive the patient data; and f) broadcasting from the one communicator the received patient data to its communicator transceiver area so that other communicators that are not located within the device transmission area but are located within the transceiver area of the one communicator are able to receive the patient data transmitted from the one patient monitoring device.

An eighth aspect of the instant invention is directed to a method of communicating information relating to physical attributes of patients that comprises the steps of: a) providing multiple patient monitoring devices each having sensor means for detecting at least one physical attribute from a patient and a transmitter for transmitting the detected physical attribute; b) associating the multiple patient monitoring devices with corresponding patients; c) providing a plurality of communicators each having a transceiver adapted to receive patient data transmitted from any one of the patient monitoring devices and to communicate with other communicators; d) locating any one of the communicators to the transmission area of one of the patient monitoring devices being used to detect the physical attributes of its associated patients; e) effecting the one communicator to receive the transmitted patient data from the one patient monitoring device; and f) effecting the one communicator to broadcast the received patient data out to its communicator transceiving area.

A ninth aspect of the invention is directed to a method of disseminating information relating to physical attributes of the patients remotely that comprises the steps of: a) associating with a patient at least one oximeter having sensor means for detecting at least SP02 of the patient, the oximeter including a transceiver or at least a transmitter to transmit patient data corresponding to the detected SP02 away from the device; b) providing a plurality of communicators, each of the communicators having a transceiver adapted to receive data transmitted from the patient oximeter when located within the transmission range of the patient oximeter, the each communicator further is adapted to communicate with other communicators; c) locating one of the communicators within the transmission range of the patient oximeter so that the one communicator receives the patient data from the patient oximeter; and d) broadcasting from the one communicator the received patient data to the other communicators that are located within the transmission range of the one communicator.

A tenth aspect of the instant invention is directed to a method of conveying information relating to physical attributes of a patient remotely in a wireless communications network environment that has a plurality of transmitting and receiving devices. The method comprises the steps of: a) associating at least one wireless sensor with a patient for detecting at least one physical attribute of the patient, the sensor including at least a transmitter; (b) transmitting patient data corresponding to the detected physical attribute out onto the network; c) locating a first communicator within the transmission range of the sensor, the first communicator having a transceiver adapted to receive the patient data transmitted from the sensor; d) broadcasting from the first communicator the received patient data out onto the network; and e) establishing communication between a second communicator and the first communicator, the second communicator not in direct communication with the wireless sensor, the second communicator having a second transceiver adapted to receive the patient data broadcast by the first communicator.

An eleventh aspect of the invention is directed to a method for disseminating information of a patient in a wireless network having a plurality of nodes. The method comprises the steps of: a) associating at least one first type node with the patient for monitoring the physical attributes of the patient, the first type node including a detector that detects at least one physical attribute of the patient and a transmitter that transmits the detected physical attribute as patient data out to the network; b) locating a plurality of second type nodes not directly associated with the patient in the network, each of the second type nodes adapted to receive signals and/or data from the first type node when moved to within the broadcast range of the first type node, each of the second type nodes further is adapted to receive signals and/or data from other second type nodes and to broadcast signals and/or data out to the network; c) moving one of the second type nodes to within the broadcast range to the first type node to receive the patient data output from the first type node; and d) broadcasting from the one second type node the received patient data out to the network so that any other second type node located within the broadcast range of the one second type node would receive the patient data output by the first type node.

A twelfth aspect of the invention is directed to a method of disseminating information of a patient in a wireless network environment that has a plurality of nodes. The method comprises the steps of: a) associating each of multiple first type nodes with a particular patient for monitoring the physical attributes of the particular patient, each of the first type nodes includes a detector that detects at least one physical attribute of the particular patient and a transmitter that transmits the detected physical attribute as patient data out onto the network; b) positioning in the network a plurality of second type nodes not directly associated with any patient; c) configuring each of the second type nodes to receive signals and/or data from the first type nodes when moved to within the broadcast range of any of the first type nodes and to receive signals and/or data from other second type nodes when within broadcast range of the other second type nodes, and to broadcast signals and/or data out to the network; d) locating one of the second type nodes to within the broadcast range of any of the first type nodes to receive the patient data output from any of the first type nodes; and e) broadcasting thereafter from the second type node the received patient data out to the network so that any other second type node located within the broadcast range of the one second type node would receive the patient data output by the first type node.

BRIEF DESCRIPTION OF THE FIGURES

The different aspects of the invention will become apparent and will be best understood by reference to the following description of the invention(s) taken in conjunction with the accompanying drawings, wherein:

FIG. 10 shows exemplar types of messages that communicate among the various communicative devices, or nodes, of the network;

FIG. 19 is a flow diagram that illustrates the process of data being aggregated in a communicator;

FIG. 20 is a flow diagram illustrating the process for updating data in the memory of a communicator;

DETAILED DESCRIPTION OF THE INVENTION

Figure 1B:
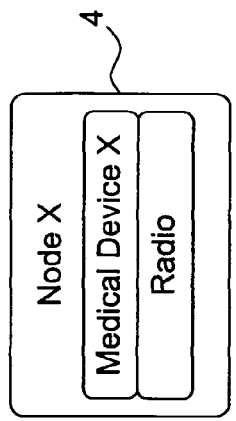
FIG. 1b is a simplified view of a node of the network, showing the node being a medical device including a radio in a medical instrumentation environment.
Figure 1A:
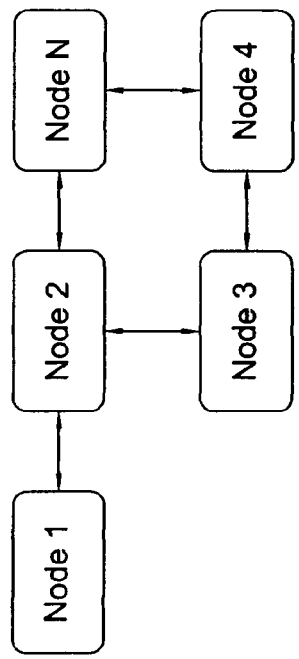
FIG. 1a is an exemplar architecture of the system of the present invention that shows an interconnected network such as for example a peer-to-peer network.

With reference to FIGS. 1a and 1b, a communications network, in the configuration for example of a peer-to-peer network, is shown. For the exemplar wireless network 2 shown in FIG. 1a, there are four nodes 1-4, as well as a node N that signifies that the network can have N number of nodes. For the embodiment of the invention shown in FIG. 1a, it is presumed that each of the nodes shown may be represented by node 4 of FIG. 1b in that each of the nodes of the network may be a medical device that includes a radio, which may be a transmitter or transceiver. The medical device may be any one of a number of devices that monitor or measure physical attributes or parameters of a patient or subject. Such medical devices include, but are not limited to, oximeters, heart rate monitors, capnographs or $CO_2$ monitors, pumps that connect to the patient and other devices that monitor particular physical attributes of a patient. For example, in the case of a pulse oximeter, the oxygen level of arterial blood ($SPO_2$) of the patient is monitored and/or measured. In the case of a capnograph, the $CO_2$, $ETCO_2$ (End Tidal $CO_2$) and respiration rate are monitored and/or measured. Some of these medical devices may be combined. For example, the assignee of the instant application currently markets a non-radio product that is a combination of an oximeter and a capnograph under the trade name CAPNOCHECK®. For the instant invention, such combination device may be fitted with a radio so as it could act as a node of the inventive network.

The radio portion of device 4 may be a transceiver, or at least a transmitter, that operates under a conventional standard telecommunications protocol such as for example the IEEE Standard 802.15.4, so that data may be transmitted from the device out to a given broadcast or transmission area of the device. As will be discussed later, there are additional components in device 4. For the time being, suffice it to say that the communications network of FIG. 1a is a network that may comprise a peer-to-peer network of devices, medical or otherwise, that can communicate among each other without a hub or a central network controller.

As will be discussed in greater detail later, the nodes of the network are time synchronized and the communications among the nodes are scheduled, so that network interference that may affect the communications among the nodes is substantially eliminated. Also, particular message types are provided to enhance the quality of communication among the nodes. The particular architecture of the network as shown in FIG. 1a further enables the dissemination of data to all of the nodes by the data being broadcast. By a process of aggregation performed in each of the nodes, the most recently obtained data is broadcast by the nodes so that the integrity of the data being communicated is enhanced. This results in the data being communicated or propagated throughout the network to be predictable, consistent, and without any need for a central controller or hub.

The topology of the network can vary and not be constrained by a particular configuration, as the size of the network may range by a minimum of 2 to a maximum of N nodes. As each of the nodes, which may be in the form of a medical device, is mobile, the topology of the network varies in accordance with the respective locations of the nodes at any one particular time. Given that each of the nodes has its own radio transmitter, each of the nodes is capable of broadcasting to a predetermined transmission range. Thus, all nodes within the broadcast or reception range of a given node can be in communication therewith. Further, as communication is not controlled by a specific node or central hub, the communications among the nodes are not restricted to a particular access point.

Figure 2:
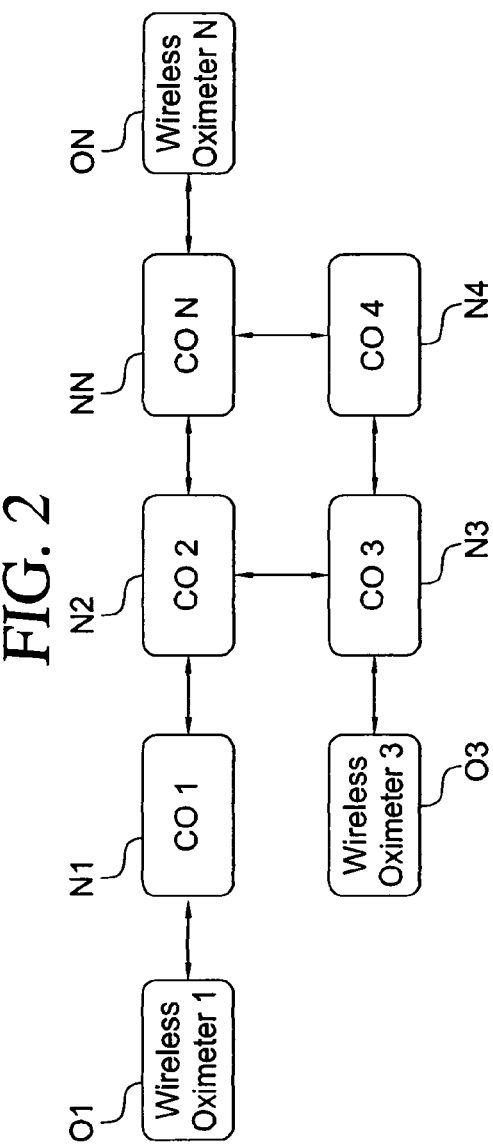
FIG. 2 is an exemplar network that combines the peer-to-peer network of FIG. 1a with wireless medical devices such as wireless oximeters that are connected to the network.

As shown in FIG. 2, the network of FIG. 1a is communicatively connected to a number of wireless oximeters, or the other medical devices discussed above. The nodes per discussed above in the FIG. 1a network are referenced as N1-NN and may also be referred to as communicators CO1-CON. For the FIG. 2 illustration, wireless oximeters O1, O3 and ON are communicatively connected to communicators CO1, CO3 and CON, respectively. For the instant invention, the wireless oximeters, or other medical devices per discussion above, that monitor physical parameters of the patient, may be referred to as a first type of nodes, while the communicator CO1-CON may be referred to as a second type of nodes N1-NN, of the network. The wireless oximeters may further be referred to as sensor or sensing nodes while the communicators may further be referred to as relay or propagating nodes.

The wireless oximeters are devices or modules that may be worn by a patient, for example on the finger, with a sensor built therein to detect the $SP02$ of the patient. An example of such wireless oximeter module is disclosed in U.S. Pat. No. 6,731,962, assigned to the assignee of the instant invention. The disclosure of the '962 patent is incorporated by reference herein. Other types of oximeter sensors that may be worn by or associated with a patient include the reflective type that may be attached to the forehead or other substantially flat surfaces of the patient, or an ear type that is adapted to clip onto the ear of the patient. The inventors have found that the inventive network operates efficiently even when 16 wireless oximeters are connected to the network. This is not to say that the FIG. 2 network may not have a smaller number of oximeters, for example 1, or more than 16 oximeters. Similarly, it was found that the preferable number of communicators or nodes in the system or network should be between 2 to 32, with the number of communicators or nodes greater than 32 being possible by adjustment of the time slots and time synchronization of the system, as will be discussed later.

Figure 3:
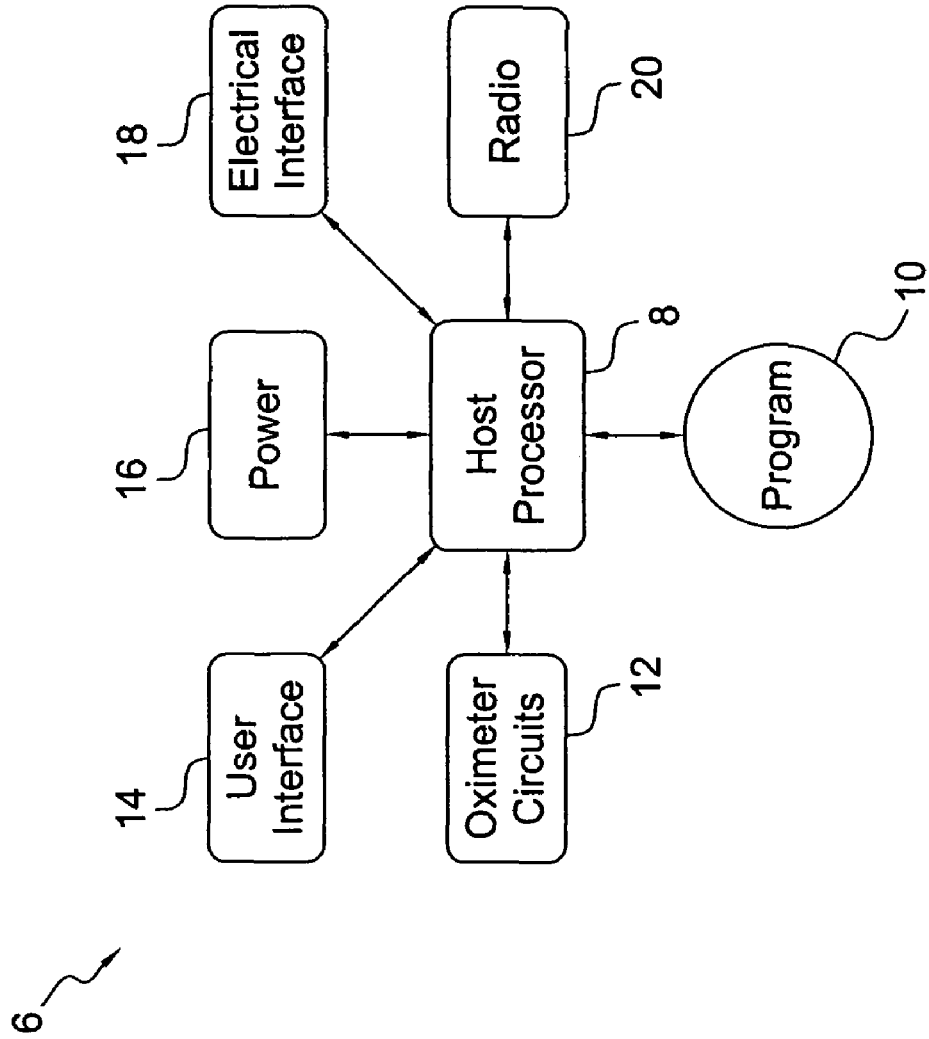
FIG. 3 is an exemplar simple block diagram of a communicator, in this instance a medical communicator, that forms a node of the network of the instant invention.

With reference to FIG. 3, a communicator 6 of the instant invention is shown to include a host processor 8 that executes a program 10 stored in a memory, not shown. The program enables processor 8 to operationally control the oximeter circuit 12, which interfaces with an external oximeter that is either coupled to the communicator by hardwire such as for example a cable, or by radio, so as to produce digital oximetry data for processing by processor 8. An user interface 14, also connected to processor 8, enables the communicator to interface with the user. The user interface may comprise a display, for example a LCD display, an input source for example a keypad, and an audio circuit and speakers that may be used for alarms. Providing the power to the communicator 6 is a power circuit 16 that may include a battery, or DC input and other well known power analog circuits, so that regulated power may be routed to all of the active circuits of the communicator. An electrical interface 18 is also provided in communicator 6. Such electrical interface may comprise an electrically conductive communications port such as for example a RS-232 port, a USB port, or other similar input/output (IO) port that allows interfacing to and from the communicator. To transceive data to and from the communicator, there is provided a radio transceiver that wirelessly transceives or communicates data between the communicator and other communicators, as well as between the communicator and a sensor device such as the wireless oximeter sensor shown in FIG. 2, or other sensor devices, medical or otherwise, that are adaptable to transmit data wirelessly.

Figure 4:
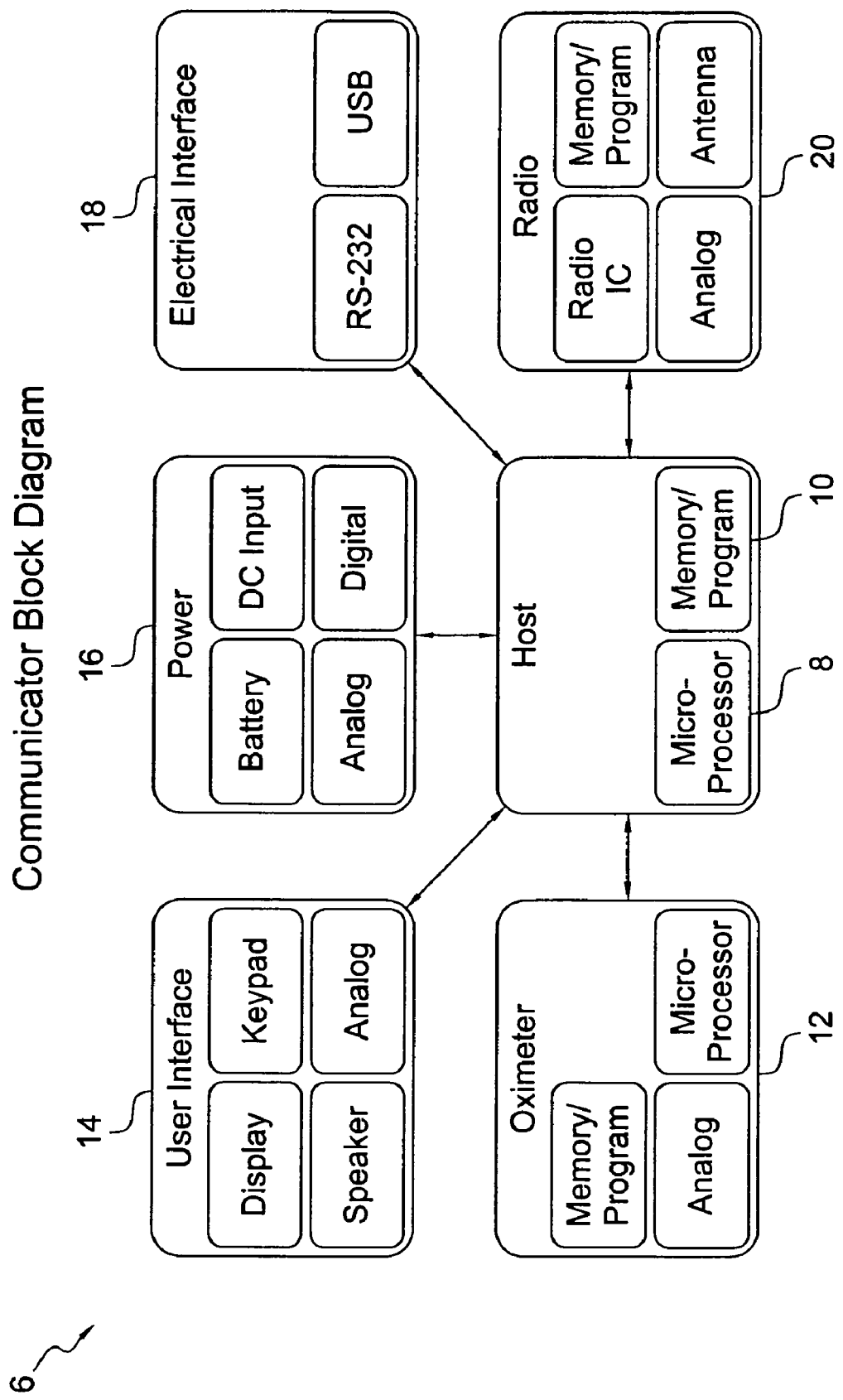
FIG. 4 is yet another block diagram in more detail of the communicator, or a relay node, of the network of the instant invention.

FIG. 4 elaborates on the various components of the communicator 6 shown in FIG. 3. For example, the user interface 14 is shown to include a display, a keypad, a speaker and an analog to digital (A/D) circuit designated by "analog". As is well known, the A/D circuit converts the analog input into a digital signal, which is sent to the host processor 8. The power component 16 of the communicator as shown in FIG. 4 includes a battery, the DC input for charging the battery, a conventional analog power circuit and a digital circuit that allows the power component 16 to communicate with host processor 8. The power provided by the power component is routed to all of the active circuits of the communicator. The electrical interface component 18, as was mentioned previously, has one or both of the RS-232 and USB ports, or other interfacing ports that are conventionally used. The oximeter component 12 has the analog circuit for analyzing the analog signals received from the patient sensor, a memory program that stores the operational functions for the oximeter component, and a microprocessor that processes the data received from the patient to produce digital oximetry data, which is then communicated to the host processor 8. As was noted earlier, a memory program 10 in the host that encompasses processor 8 provides the operational instructions to processor 8 for the overall operation of the communicator. The last major component in communicator 6 is the radio 20, which includes a radio IC module, a memory stored program that controls the functioning of the radio transmitter, the analog circuits for controlling the operations of the radio and the antenna that allows the radio transceiver to transmit and receive signals to and from the communicator.

Figure 5:
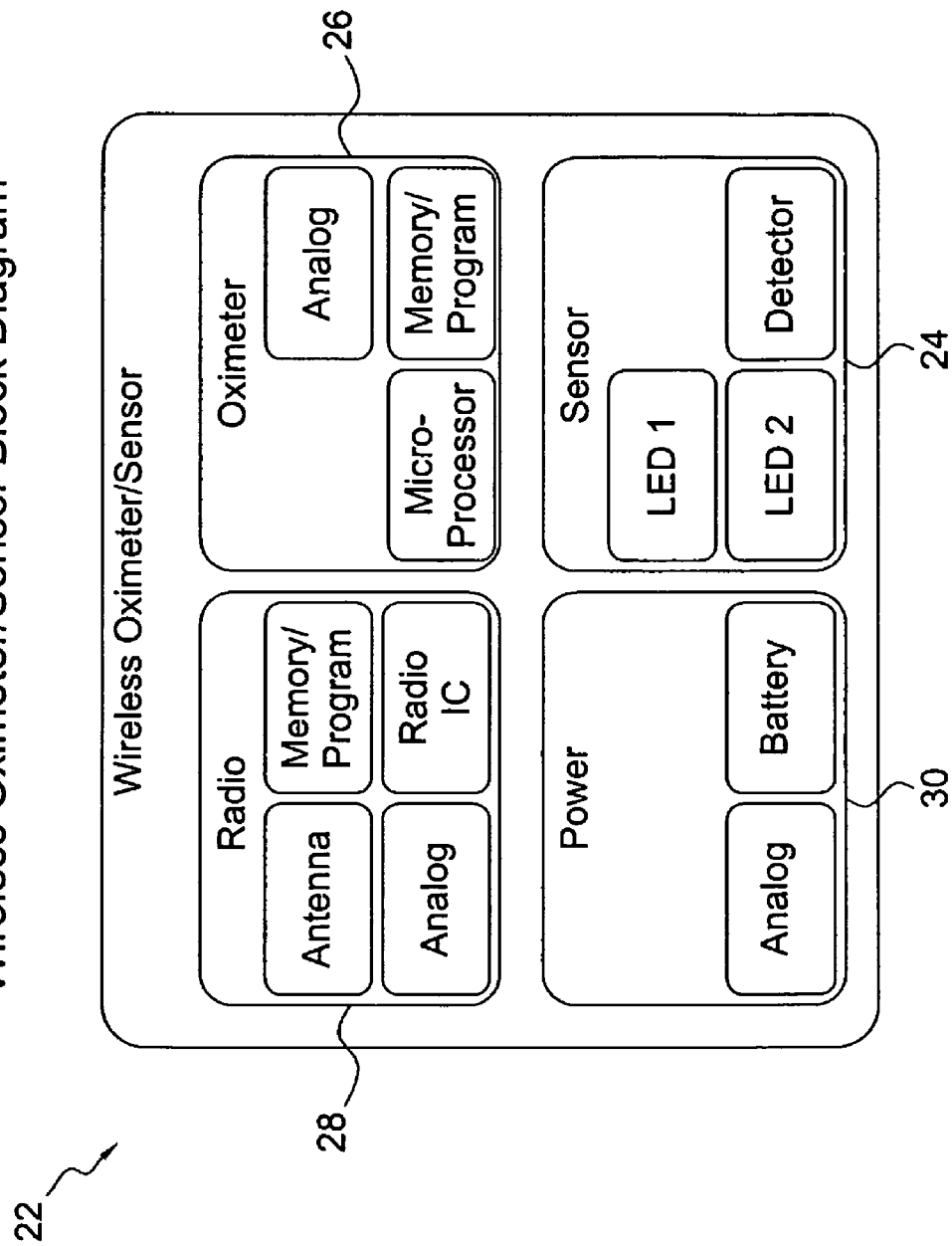
FIG. 5 is a block diagram of the wireless oximeter sensor, or the sensor node, that forms part of the communication network of the instant invention.

A wireless oximeter device that forms the sensor node of the network is shown in FIG. 5. The wireless oximeter 22 is shown to include a sensor component 24. Such component is conventional and includes two LEDs that output lights of different frequencies to a digit or some other area such as the forehead of a patient, and a detector that detects the light that passes through or reflected from the patient. Also included in wireless oximeter 22 is an oximeter circuit 26 that includes a processor, an analog circuit that analyzes the waveform signals detected from the patient and a memory that stores the program to instruct the analog circuit to analyze the incoming signals from the patient and converts it into oximetry data. The operation of the sensor 24 is also controlled by oximeter circuit 26. Interfaced to and working cooperatively with the oximeter component 26 and/or the sensor component 24 is a radio component 28 that includes an antenna, a program stored in a memory, an analog circuitry that operates the radio IC module and an antenna that transmits the oximetry data of the patient to the communicator. Power component 30 includes the battery power source and the conventional analog power circuitry that supplies power to the other components of the wireless oximeter. In the network of the instant invention, per shown for example in FIG. 2, the wireless oximeter device of FIG. 5 transmits collected patient data to the communicator(s) that is/are within its broadcast range, or transmission area.

Figure 6:
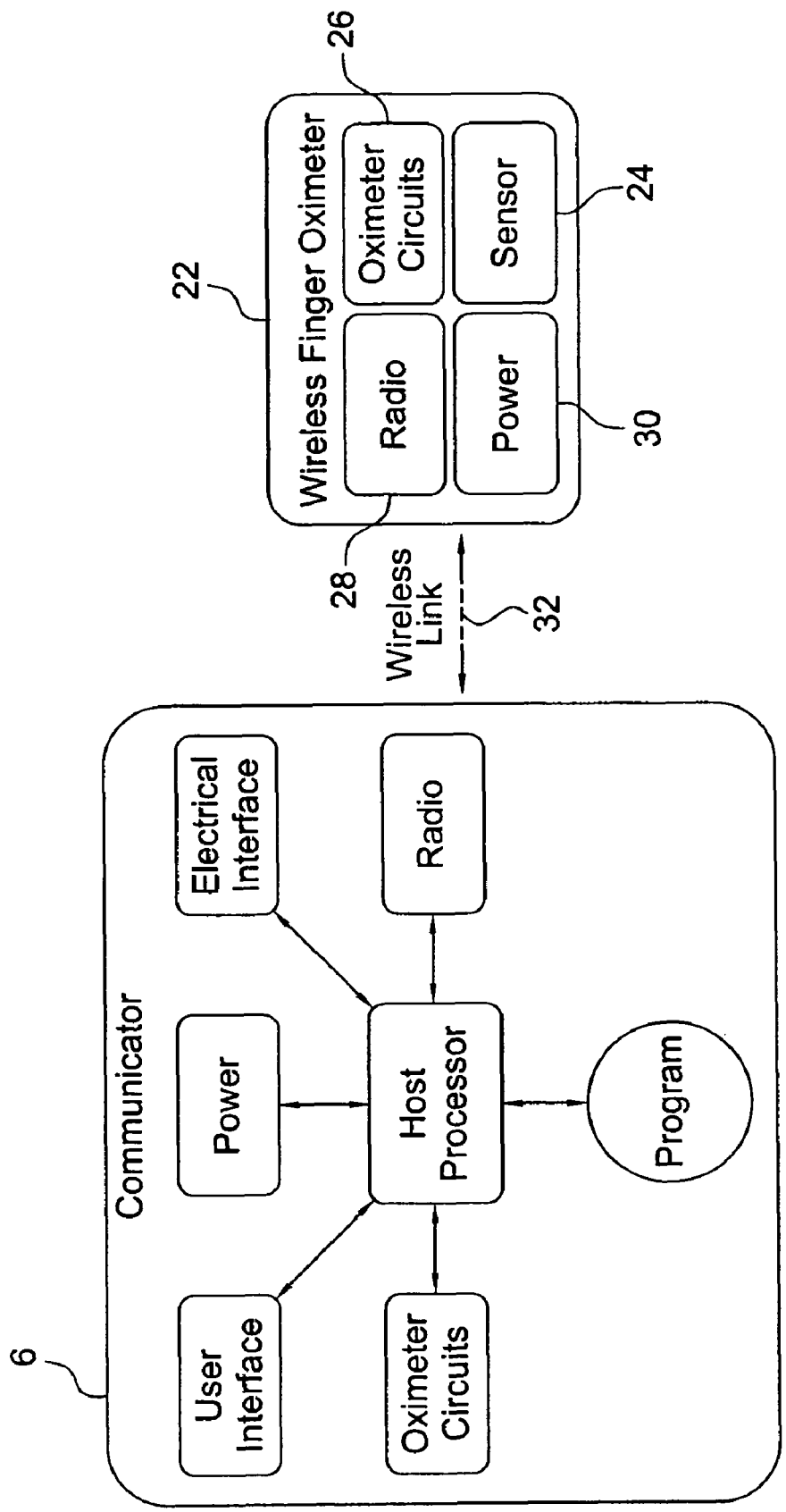
FIG. 6 shows a communicator of the instant invention, acting as a relay node, being communicatively linked to a wireless oximeter, or a sensor node, of the instant invention network.

FIG. 6 shows in more detail the interaction of a wireless finger oximeter device with a communicator of the instant invention. Here a wireless communications link 32 is established between communicator 6 and the wireless oximeter 22. As shown, the radio transceiver of communicator 6 communicates with the radio transmitter of oximeter 22, so that the oximeter data obtained from the patient by sensor 24 is sent to communicator 6, which may then relay the information by broadcasting it out to its transceiver area. It should be noted that communicator 6 would receive the data from oximeter 22 only if it is within the transmission area or broadcast range of the oximeter device. For the FIG. 6 embodiment, when the oximeter circuit in the wireless oximeter 22 is actively analyzing and converting the patient data, the oximeter circuit in communicator 6 may not be since the patient data is being transmitted from oximeter device 22 to communicator 6. The signal being transmitted from oximeter device 22 to communicator 6 is in most instances a digital signal. However, there may be instances where raw data may be sent directly from the oximeter device to the communicator, if it is desirable to eliminate the analog to digital circuitry in the oximeter and also reduce the processing power from the oximeter. In other words, raw data may be sent from an oximeter device to a communicator, if necessary, so that the communicator may perform the processing that converts the raw data into the required oximetry data.

Figure 7:
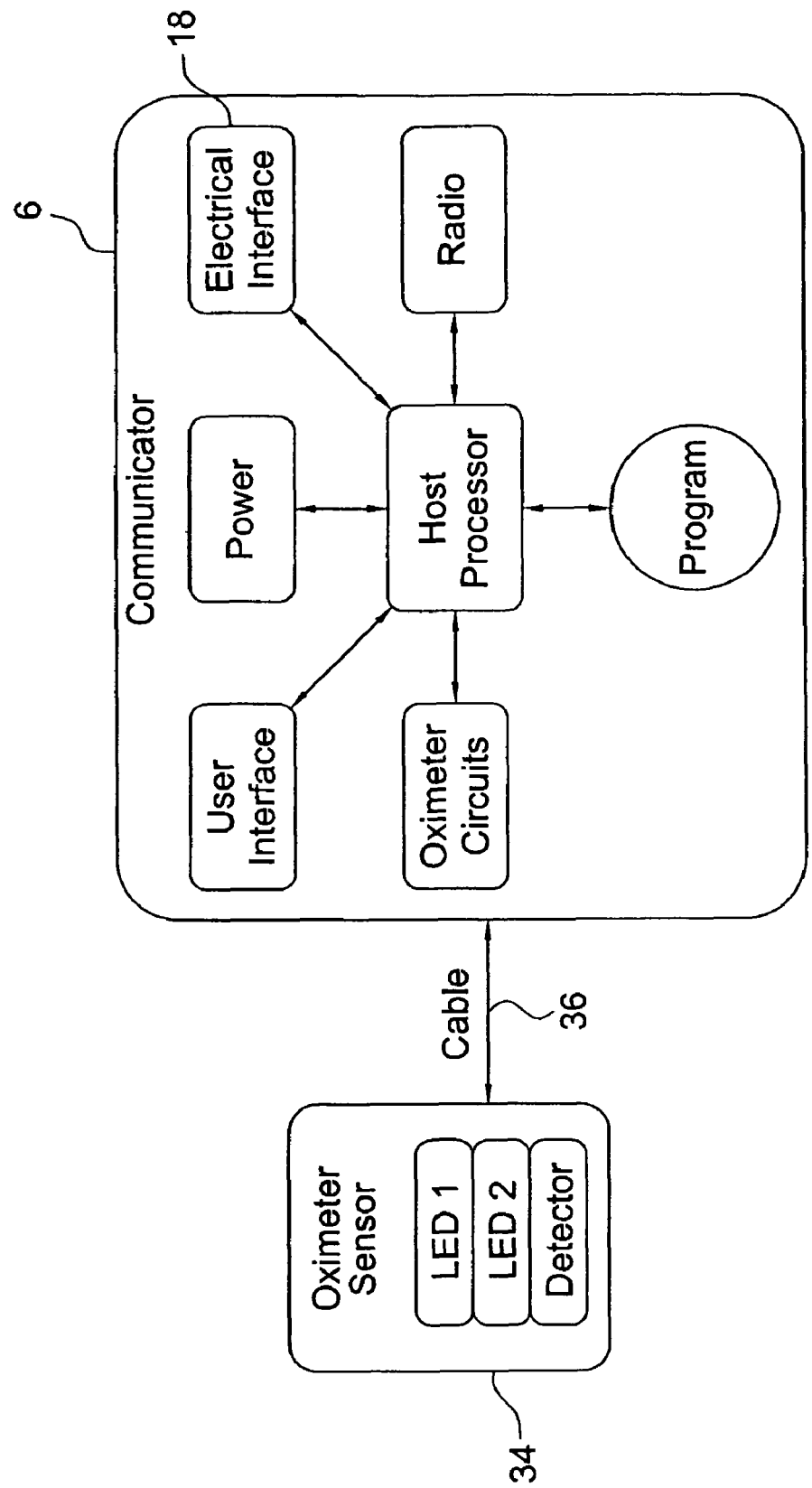
FIG. 7 is a block diagram showing a sensor, in this instance an oximeter sensor, being hardwire connected by a cable to a communicator of the instant invention, so that the communicator may act as a transmitter for the sensor.

In place of the wireless finger oximeter device 22 shown in FIG. 6, the instant invention is also adapted to be used with a conventional oximeter sensor, such as 34 shown in FIG. 7. There, a conventional oximeter sensor that has the light source and the detector necessary for measuring the SP02 of the patient is connected by means of a cable 36 to a communicator of the instant invention. This may be effected by mating the electrical connector of the sensor to the port that is a part of the electrical interface 18 of communicator 6. The signals received from the patient are then processed and stored, and then broadcast out by the communicator to its transceiving area. In this embodiment, communicator 6 acts as the transmitter of the patient monitoring device by working cooperatively with the oximeter sensor. Moreover, as it has to be within cable distance from oximeter sensor 34, communicator 6 is located fixedly relative to the oximeter sensor and proximate to the patient.

Figure 8:
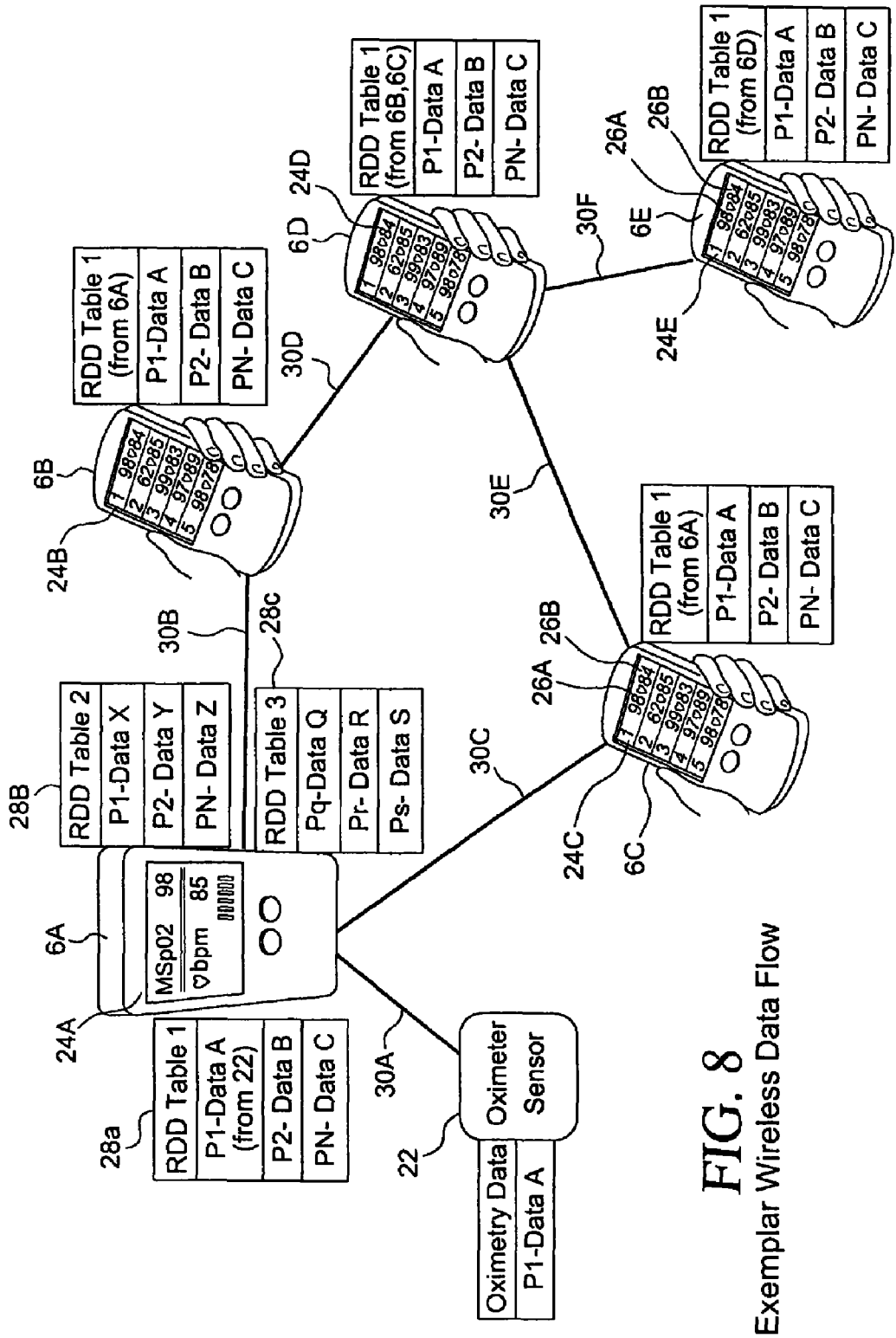
FIG. 8 is an illustration of an exemplar system of the instant invention whereby a patient sensor is communicatively linked to a communicator, which in turn is communicatively linked to other communicators of the network.

FIG. 8 shows an ad hoc mesh communications network of the instant invention where a wireless oximeter sensor device 22, with the sensor possibly attached to a digit of a patient, not shown, being in communication with a communicator 6a. Communicator 6a in turn is in communication link with communicator 6b and communicator 6c. Both communicators 6b and 6c are in communication link with communicator 6d. Communicator 6d is also communicatively linked to communicator 6e.

As further shown in FIG. 8, each of the communicators has a display 24 that is capable of showing the data of multiple patients. For the exemplar communicators of FIG. 8, both the SP02 and the heart rate of the patient(s) are shown on displays 26a and 26b, respectively. Further, there are shown on each of the displays of exemplar communicators 6b to 6e five sets of data, with each set of data representing a particular patient. Although data representing five patients is shown in the exemplar communicators of FIG. 8, it should be appreciated that a smaller or a greater number sets of patient parameter data may also be displayed by each of the communicators. Furthermore, it should be appreciated that if the communicators of FIG. 8 were devices other than oximeters as mentioned supra, then the display of each of those communicators may display patient data that represents other patient attributes, such as for example CO2 and respiration rate in the case where the devices are CO2 monitors or combined CO2 monitor and oximeter devices.

For the wireless oximeter sensor 22 that is communicatively connected to communicator 6a, the physical parameter measured or sensed from the patient 1 may be sent as an oximeter data message data file, 96 byte for example, to communicator 6a. Upon receipt of the data file from oximeter device 22, communicator 6a stores the data file for patient 1 as P1 in its remote data display RDD table 28a. The patient 1 previously stored data in the memory of communicator 6a is replaced or updated by the latest data from patient 1. The RDD table 28a for the exemplar communicator 6a is shown to have a capacity that can store data of a plurality of patients, for example from patient P1 to patient PN. An exemplar approximately 18 byte memory may be reserved for each of the patients in the memory store of the communicator. Multiple tables may be stored in each of the communicators, so that patient data that were received at different times may actually be kept and compared with the latest information for an aggregation process that will be later described in greater detail. The additional exemplar tables 28b and 28c for the communicator 6a are shown in FIG. 8.

The interactions between wireless oximeter 22 and communicators 6 begins when wireless oximeter 22 transmits a signal representing at least one physical attribute of the patient, for example the patient's SP02, away from the oximeter to a predetermined transmission range, i.e., the sensor's transmission area. For the FIG. 8 exemplar network, the wireless oximeter 22 may be considered the sensor node. As illustrated by communications link 30a of the FIG. 8 network, communicator 6a is located within the transmission area or zone of wireless oximeter 22. Thus, when wireless oximeter 22 outputs the patient data sensed from patient 1, communicator 6a would receive the patient data being transmitted. Upon receipt, the patient data may be stored in a RDD table, for example 28a, as patient data P1. If there was prior P1 data for patient 1, this prior data is replaced by the just received data in the RDD table. The stored data may be displayed on display 24 of communicator 6a as the SP02 and/or pulse rate of the patient. Note that the patient data may also be displayed, analyzed, conductively communicated, and/or stored for trending, RDD or high speed application.

As further shown in the exemplar FIG. 8 network, communicator 6a has established communication paths with communicator 6b and communicator 6c via communication links 30b and 30c, respectively. As was discussed previously, each of the communicators of the instant invention has its own radio transceiver, so that each communicator is adapted to receive signals from both wireless oximeters or other medical sensors and other communicators, so long as it is within the transmission range of those sensors and/or communicators. Conversely, each of the communicators is adaptable to broadcast a signal out to a predetermined broadcast range, or its transceiving area. Thus, for the exemplar network of FIG. 8, as each of communicator 6b and 6c is within the transceiving area of communicator 6a, those communicators each are in communication with communicator 6a.

For the exemplar network of FIG. 8, upon receipt of the patient P1 data from wireless oximeter 22, after storing the received data in its RDD table 28a, communicator 6a broadcasts this latest P1 data out to its transceiving area. Communicators 6b and 6c, each being within the transmitting range of communicator 6a, receive the same data of patient P1. Each of those communicators 6b and 6c then updates its own RDD table, and may display the latest patient P1 data on its display, so that the holder of those communicators could see the physical parameters, in this instance, the SP02 and pulse rate, of patient P1. Each of communicators 6b and 6c then transmits the latest patient P1 data out to their respective transceiving areas. Note that each of communicator 6b and 6c is shown not to be in direct communications link with wireless oximeter sensor 22.

As communicator 6d happens to be in the transmission range of both communicators 6b and 6c, it receives the data of patient P1 from each of those communicator via communication links 30d and 30e, respectively. In this scenario, as the patient P1 data is the same from both communicators 6b and 6c, any updating of the data relating to patient P1 results in the same data being updated in the RDD table of communicator 6d. However, in another scenario where the communications schedule between communicators 6b and 6d is substantially different from that between communicators 6c and 6d, it may be that the data from the same patient received by communicator 6d from communicators 6b and 6d may differ due to the propagation delay of the patient data along the respective communications links. In that case, the later patient data is stored as the patient data in communicator 6d. To prevent conflict in the event that the transmission of data from multiple nodes takes substantially the same amount of time, a time slotted schedule communication protocol, which will be discussed later, is provided for the network of the instant invention. The last node in the exemplar network of FIG. 8 is communicator 6e, which is in communications range with communicator 6d via communication link 30f. Communicator 6e is not in communication range with any of the other communicators or the wireless oximeter sensor 22. With the instant invention, even though communicator 6e is located remotely from sensor 22, the holder of communicator 6e nonetheless is able to monitor the physical parameter of patient 1 due to the propagation of data, or data hop, of the RDD messages across the communicator nodes of the network.

Although only one wireless oximeter sensor 22 is shown in the exemplar network of FIG. 8, it should be appreciated that there might be multiple wireless oximeter sensor devices linked communicatively along the network, so that different communicators of the network may transmit patient information to other communicators communicatively connected thereto. As a result, data of multiple patients may be displayed on each of the communicators. This is illustrated by the respective displays 24 of communicators 6b, 6c, 6d and 6e of the FIG. 8 network where five sets of data, each corresponding to a particular patient, are displayed on each of those communicators. The users or operators of those communicators may each therefore be able to monitor the physical parameters of a number of patients, even though they may not be in the vicinity of any one of those patients. Thus, for the network of the instant invention, so long as a remote communicator node is within the broadcast range of another communicator node that in turn had received, via possibly other communicator nodes, the data from a patient, that remote communicator node would also be in receipt of the same patient data and can therefore monitor remotely the well being of that patient.

Figure 9:
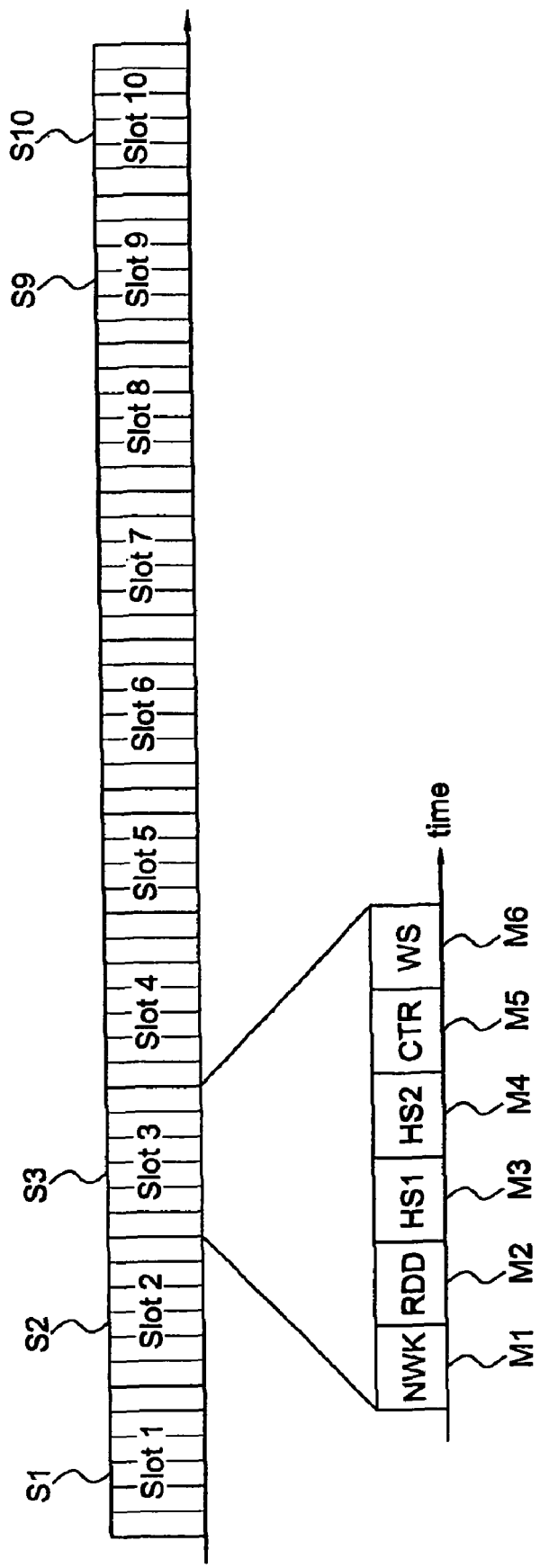
FIG. 9 is an exemplar illustration of the time slots for scheduling communications among the various communicative devices of the network.

To prevent conflict among the various nodes of the network of the instant invention, a time slotted scheduled communication protocol is mandated. To that end, each of the devices, or nodes, of the network has one slot of a given time period to transmit its data. This time slotted schedule communications protocol is illustrated in FIG. 9. As shown, a number of slots, for example slots S1 to S10, are provided in the exemplar time period of FIG. 9. The number of slots may correspond to the number of communicator devices in a particular network. Thus, if the network were to include 16 devices, then there would be 16 slots provided in the time period. The time periods are repeated so that communications among the various devices in the network are scheduled. Predictable and reliable network communications result.

For each device, the time slot assigned thereto enables the device to transmit multiple messages exclusively at that given time slot. For example, for the exemplar network of FIG. 8, slot S1 may be assigned to communicator device 6a, slot S2 to communicator 6b, slot S3 to communicator 6c, slot S4 to communicator 6d and slot S5 to communication 6e. Thus, communicator 6a would transmit at time slot S1, communicator 6b at time slot S2, communicator 6c at time slot S3, etc. For the exemplar network of FIG. 8, it may not be necessary to have 10 slots for each time period. One possible way of assigning each device a particular slot is for the operator of the facility that the network is located, for example an ICU ward in a hospital, to have programmed into the devices their respective slots. Another possible way is for the operator of the network to assign the devices the different slots. The various devices in the network are synchronized to the radio frequency (rf) transmissions.

There is a fair amount of data that needs to be transmitted in pulse oximetry, including wireless oximetry. In addition to the number of devices in the network, the number of messages may be selectively optimized for each of the slots. In the communications protocol of FIG. 9, it is assumed that there might be six types of messages that are transmitted at their assigned slots by each of the relay node devices. These messages are in the form of message packets and are illustrated in FIG. 10. In FIG. 9, the messages (M) are labeled, with M1 corresponding to the first message NWK and M6 corresponding to the last message WS. Message M1, the NWK message, refers to a node overhead information message, or the "network overhead information". Message M2 is the RDD (remote data display) message that carries the data stored in the RDD table in the memory of the communicator and, once updated, may be displayed by the communicator. Messages M3 and M4 are the HS1 (high speed 1) and HS2 (high speed 2) messages that flood or broadcast data, when needed, to the other node devices in the network.

To illustrate with reference to the FIG. 8 exemplar network, if the patient data received from the patient (P1) indicates to communicator 6a that the data from the patient is outside of a predetermined specified or acceptable range, then communicator 6a would go into an alarm mode in which an alarm is set off, so that the user of communicator 6a knows that there is something amiss with patient P1. At the same time, to overcome the bandwidth limitations of the network, by means of HS1 and/or HS2 messages, communicator 6a floods the network with alarm messages in order to reach the other communicators in the network, since this may be an emergency situation where the people who are carrying the other communicators should be notified. Thus, by sending HS1 and HS2 messages, the operators or medical personnel of communicators 6d and 6e, who are not in direct communications link with the wireless oximeter sensor 22, are nonetheless notified of the alarm condition for patient (P1) so that appropriate action, if any, may be taken by those healthcare personnel. Also, the HS1 and/or HS2 messages may be selectively used to broadcast, upon request by a user, measured physical attribute(s) at a high rate to a remote communicator. The user may either be the person associated with the communicator that is to transmit the data, or the person associated with the remote communicator to which the data is to be transmitted. In the event that the request to use the HS1 and/or HS2 messages were to come from the remote communicator, a remote request first has to be received and recognized as such by the transmitting communicator.

The next message M5 (CTR) is a control message from the communicator to its dedicated wireless sensor, which is identified by message M6 WS (wireless sensor). This is required because a wireless sensor may not have the user control mechanisms required to configure the integral radio and oximeter. Furthermore, a communicator node in the network may not necessarily be in direct communications link with its dedicated sensor. For example, it may be that the carrier of communicator 6e is in fact the responsible nurse for the patient who is connected to wireless oximeter sensor 22 in the FIG. 8 exemplar network. And the reason that communicator 6e is not in the vicinity of wireless oximeter sensor 22 may be that the nurse had to take care of another patient and accordingly had moved out of the transmission range of wireless oximeter sensor 22. Yet the nurse nonetheless is able to continuously monitor the physical parameters, for example the SP02 of patient P1 due to the relaying of the patient P1 data from the other communicators of the network. Message M6 therefore identifies to the other communicators that wireless oximeter sensor 22 is the dedicated sensor for communicator 6e. Each communicator may also control the operation of its dedicated wireless oximeter, if the wireless oximeter is adapted to wirelessly communicate bidirectionally, by sending a M5 control message CTR, which is relayed by the other nodes in the network to the wireless oximeter identified by the WS message.

With the time slotted scheduled communications protocol shown in FIG. 9, the communications among the various devices of the network become predictable and reliable. Accordingly, the protocol provides a deterministic approach for the instant invention system or network, as the processes for the various nodes are synchronized. Moreover, the system is deterministic in that each time slot is assigned to a particular device, so that each device may be able to listen to the other devices when it is not its time to "talk"; and when it is the device's turn to "talk", the other devices of the network would listen. In other words, each of the devices of the network has been assigned or allotted a given time period to communicate or disseminate information to the other devices of the network, without any central controller mandating the various devices what to transmit and when to transmit.

The message packets of the message types of FIG. 9 are assigned a sufficient size, for example 96 bytes, so that all necessary data may be carried in those message packets for propagation across the network. The message types and the respective flows of those messages across the network are shown in more detail in FIG. 10. There, communicator is designated "CO".

Figure 11:
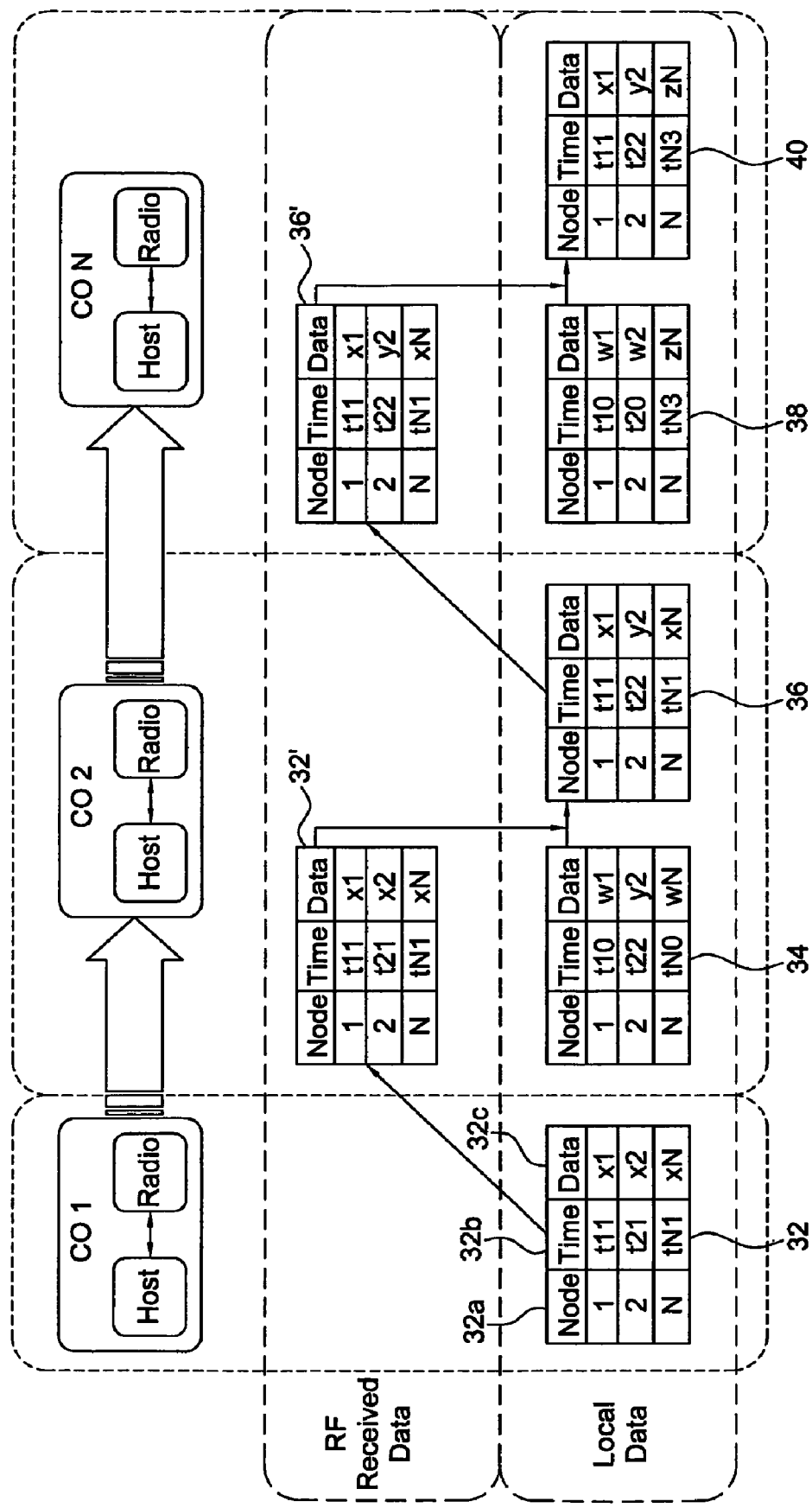
FIG. 11 is an exemplar illustration of how the messages are aggregated and broadcast from one node communicator to another node communicator in the network.

FIG. 11 illustrates how the remote data display messages are aggregated and broadcast or flooded to the various relay nodes or communicators in the system and network of the instant invention. Here it is assumed that there are multiple communicators (CO1, CO2 to CON) in the network, with each of the communicators transmitting its RDD message out to a given transceiving range, or broadcast range. As shown, communicator CO2 is within the broadcast range of communicator CO1 and communicator CON is in communication range with at least communicator CO2. To prevent confusion and to enhance understanding, for the discussion of FIG. 11, "RDD" may refer to a memory table in each of the communicators and also a message when it is transmitted from one node communicator to another node communicator.

Communicator CO1 has in its memory a local data store that stores the RDD message as RDD table 32, which communicator CO1 had incorporated therein the information it received, either directly or indirectly, from a wireless oximeter. For RDD table 32, "Node" 32a refers to the nodes, both sensor and communicator, of the network, the "Time" 32b refers to the time stamp of when the message was recorded in the node, and the "Data" 32c refers to the kind of data that was transmitted from the node and received by the communicator. Thus, the RDD table in communicator CO1 has stored therein data from a number of nodes (1, 2 to N) each having corresponding data (x1, x2, xN) with a given time stamp (t11, t21 to tN1), respectively. The RDD table 32 from communicator CO1 is broadcast by the radio transceiver of the communicator to its transceiving range and is received as RDD message 32' by communicator CO2.

Communicator CO2 also has a previously stored RDD table that has a number of sets of data from the various nodes, per shown by RDD table 34. An aggregation process next takes place in communicator CO2 in that the data received from communicator CO1, i.e., from RDD message 32', is compared with the prior stored data in RDD table 34. As an illustration, the previously stored information from node 1 is "t10" in RDD table 34, whereas the information for node 1 in RDD message 32' has a time stamp "t11". This means that the information relating to node 1 is more recent in RDD message 32'. As a consequence, the data for node 1 is updated to "x1" and is stored in the new RDD table 36. The same aggregation process takes place with the information relating to node 2. For that node, insofar as the time therefor in RDD table 34 is "t22" whereas the time for node 2 in RDD message 32' is "t21", the data that is stored in RDD table 34 is judged to be the more recent data. Accordingly, the data "y2" in RDD table 34 is copied to RDD table 36. The same aggregation process repeats for the remainder nodes in RDD table 34 by comparing its previously stored data with those in RDD message 32'. Once the data in the RDD table 34 has all been compared and if needed updated, the updated RDD table 36 is broadcast as RDD message 36' by communicator CO2 out to its transceiving area.

RDD message 36' is received by communicator CON as RDD table message 36'. The same aggregation process then takes place in communicator CON whereby the information in RDD message 36' is compared with the previously stored information in RDD table 38 for generating an updated RDD table 40. For the example illustration in FIG. 11, the data for node 1, as received by communicator CO1, is relayed to communicator CON and updated in its RDD table 40. Further, the data for node 2, as reflected in RDD table 40 of communicator CON, is updated from the data previously stored in RDD table 34 of communicator CO2.

In a system where all of the communicators are within range of all of the other communicators, there would be minimal latency in terms of the messages transmitted and received. However, in practice, such often is not the case as shown in exemplar FIG. 8, so that there is always a propagation delay in terms of the messages that are being broadcast from one communicator to the next one, as the RDD messages would "hop" from one communicator node to the next communicator node, in order to propagate across the network. Even though only RDD messages are disclosed so far as being propagated across the network, it should be appreciated that messages aside from or in addition to RDD messages may also be disseminated or propagated across the network from node to node. For example, the communicators have built-in alarm functions, so that if the physical parameter(s) measured from a patient exceeds or falls below respective upper and higher limits, i.e., outside predetermined safety limits, the alarm is triggered to warn the user of the communicator that something may be amiss with the patient. Another aspect of the instant invention is that instead of RDD messages, only an alarm signal is propagated or flooded across the network to warn the various people, medical personnel or otherwise, equipped with communicators that a particular patient may be in distress.

So that additional information may be propagated across the network, the communicators each may be fitted with a text messenger chip so that its display may be actuated to a text mode to receive text messages that may accompany the alarm, which may be a sound of a given frequency or loudness or a flashing screen for example. The text message may be specifically directed to a given communicator, or may be broadcast or flooded to all communicators along the network. The communicator of the instant invention is therefore adapted to be used as a pager that can either simply receive an alarm from a particular patient or multiple patients, or as a more sophisticated pager where text messages may accompany an alarm when the being monitored physical parameter(s) of a particular patient or a given number of patients is/are deemed to be irregular and warrants closer scrutiny.

Power consumption is an important consideration in oximetry, since the wireless oximeters are relatively small and yet may require substantial power to operate their radio transmitters. There is therefore a need for the wireless oximeters to conserve their energy. For the network of the instant invention, since each oximeter sensor is programmed to communicate only in a given time slot assigned to it in a given time period, the wireless oximeter does not need to be cognizant of what happens to the other time slots. The wireless oximeter can therefore go into a sleep or suspension mode to conserve its power when it is not in its communication mode. But during the time that the wireless oximeter is in operation, it is important that it be synchronized with the communicators, or at least the communicator that is in range of its signals, and be able to broadcast the information that it senses from the patient to whom its sensor is attached. The time slotted schedule communications protocol of the instant invention allows such conservation of energy due to its deterministic characteristics.

Figure 12:
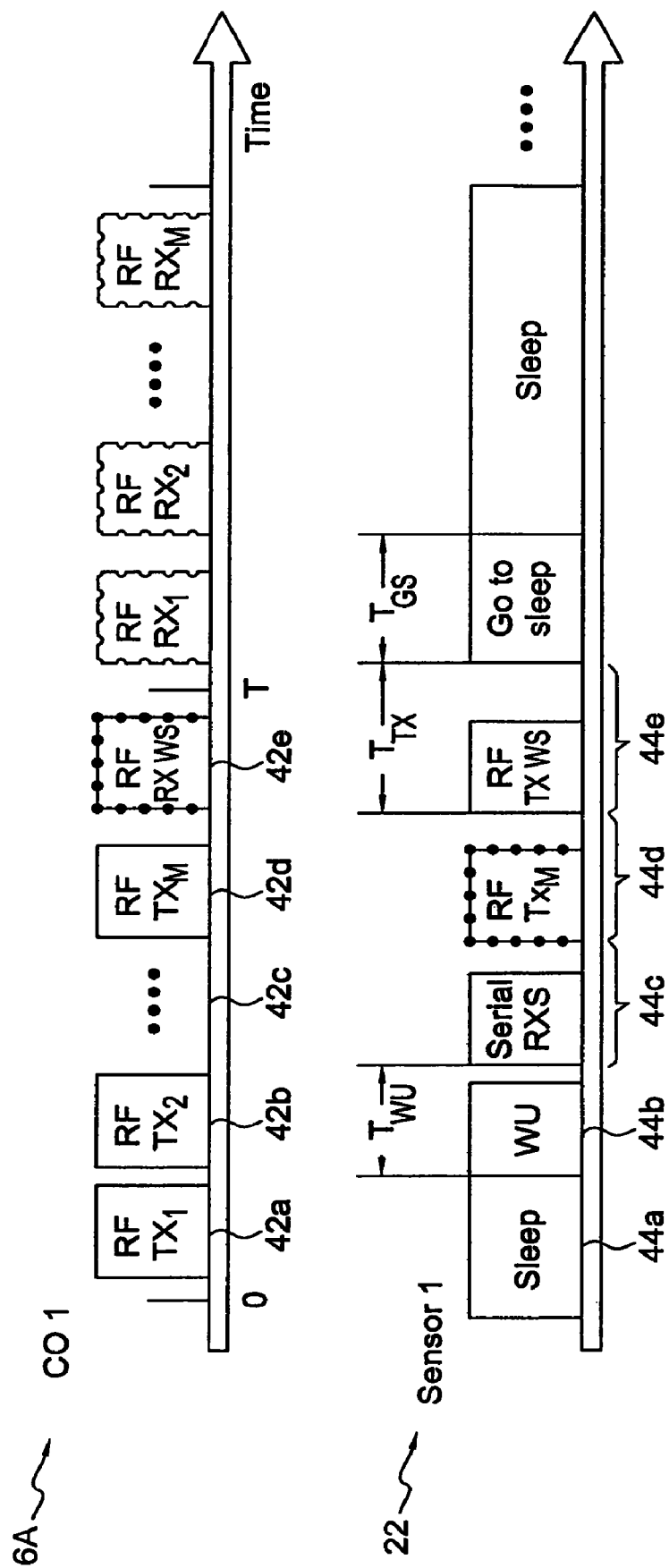
FIG. 12 is an exemplar illustration of the interactive communications between an exemplar communicator, or relay node, and a wireless oximeter, or sensor node, of the network.

With reference to FIG. 12, the interactions between a wireless oximeter sensor and a communicator are shown. The sensor and the communicator shown in FIG. 12 may be wireless oximeter 22 (Sensor 1) and communicator 6a (CO1), respectively, as shown in FIG. 8. For the communicator CO1, FIG. 12 shows the time slot (0 to T) that the communicator has been allotted for transmitting its messages. For Sensor 1, FIG. 12 shows a sequence of functions that the oximeter goes through during approximately the same time period to conserve power.

As shown in FIG. 12, at time 42a, communicator CO1 is transmitting, for example the RDD message and other transmissions disclosed with reference to FIGS. 9 and 10. At the same time 44a, Sensor 1, which is connected to a patient, is in its sleep mode. At time 42b, communicator CO1 continues to transmit its data. At time 44b, Sensor 1 wakes up either in response to an internal timer or from the initialization of the sensor to begin collecting the physical parameter(s) from the patient. This wake-up time is referenced as $T_{WU}$ in FIG. 12. At time 42c, communicator CO1 continues to transmit its data. In the corresponding time 44c, Sensor 1 receives the patient data serially from its sensor. At time 42d, communicator CO1 transmits a signal to a particular wireless oximeter, for example Sensor 1. At corresponding time 44d, Sensor 1 receives the radio frequency signal from communicator CO1 and, noting that it is a signal specifically identifying it, synchronizes its timing with that of communicator CO1. Thereafter, at time 44e, Sensor 1 transmits the data that it has obtained from the patient. This data is received by communicator CO1 at time 42e, as designated by the RX WS (receive wireless sensor) signal. Thereafter (after time T), communicator CO1 enters into a receiving mode where it listens to the various oximeters and communicators that may be present in the network, for example the $RX_1$, $RX_2$ to $RX_M$ devices. At approximately the same time, Sensor 1 goes to its sleep mode ($T_{GS}$) and stays asleep until it is either waken up by an internal timer or activated to begin monitoring the physical parameter, for example SP02, of the patient.

By thus putting the wireless oximeter sensor to sleep when it is not measuring the physical parameters from the patient, the power required for the oximeter is reduced and therefore the size of the oximeter may be reduced. On the other hand, the radios of the communicators, which are mobile units, would remain awake in order to listen in on the other communicators, and other devices, that form the nodes in the network.

For the alarm pager aspect of the invention discussed earlier, it should be noted that such pager would only need to listen in on the information that is propagating along the network. In other words, a communicator operating in the guise of a pager does not need to transmit any information. Thus, a pager communicator does not do the function of a communicator described thus far. But a communicator does do, as one of its functions, the paging function by receiving the data being propagated along the network and looking for any alarm conditions. Putting it another way, a communicator is bidirectional in terms of its communicative functions, whereas the pager does not need to be.

Figure 13:
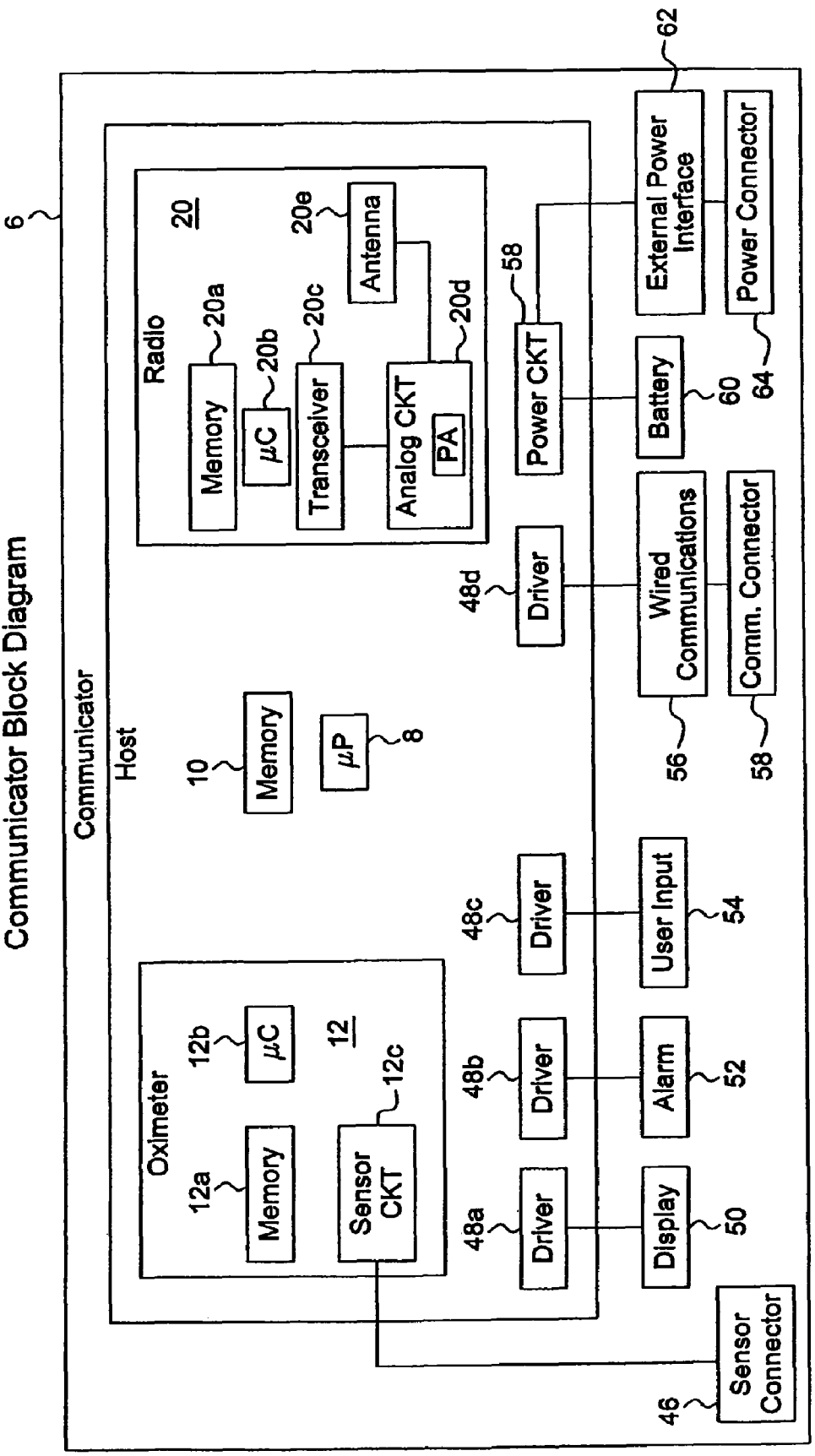
FIG. 13 is a block diagram showing in more detail the various components of a communicator of the instant invention.

With reference to FIG. 13, a more detailed block diagram of the communicator of the instant invention is shown. The same numbers that were used for the FIG. 4 block diagram are used herein for the same components. As shown, communicator 6 has a main host board or module that has an oximeter module 12 and a radio module 20. In the oximeter module 12, there is a memory 12a, a processor controller 12b that is dedicated for the oximeter module and a sensor circuit 12c. Sensor circuit 12c is connected to a sensor connector 46 to which a sensor attached to a patient may be connected by means of a cable. The radio module 20 of the communicator also has its dedicated memory 20a, a dedicated processor controller 20b, a transceiver 20c, and an analog circuit 20d that drives the signal to an antenna 20e for transceiving data to and from the communicator.

On the main host board, there is a memory 10 and a microprocessor 8 which controls all of the modules as well as the drivers on the host board or module of the communicator. Processor 8 obtains the oximetry data from the oximeter module or circuit. This data may be communicated by visual display, audio alarms, wired communications, and RF communications. As shown, there are four different drivers 48a, 48b, 48c and 48d. Driver 48a drives a display 50 that displays for example the SPO2 and the pulse rate of a patient, and possibly text messages in addition, when information more than the SPO2 and pulse rate are desired or when the communicator is being used as a pager. Driver 48b drives an alarm 52 which triggers when the measured patient parameter is deemed not to be within an acceptable range. Driver 48c drives an user input 54 such as for example a keypad or a pointing device to allow the user to interact with the communicator. Driver 48d works with a wire communications module 56, which in turn has connected thereto a communication connector 58 that may for example be an RS-232 port or a USB port as was discussed previously.

The power of the communicator is provided by a power circuit 58 that regulates the power level of a battery 60. An external power interface 62 connects to the power circuit 58 to a power connector 64, so that external power may be provided to either recharge battery 60 or to power the communicator from a power outlet, as for example when the communicator is connected by cable to a sensor that is attached to the patient. The software program for the functioning of the communicator is stored in memory 10.

Figure 14:
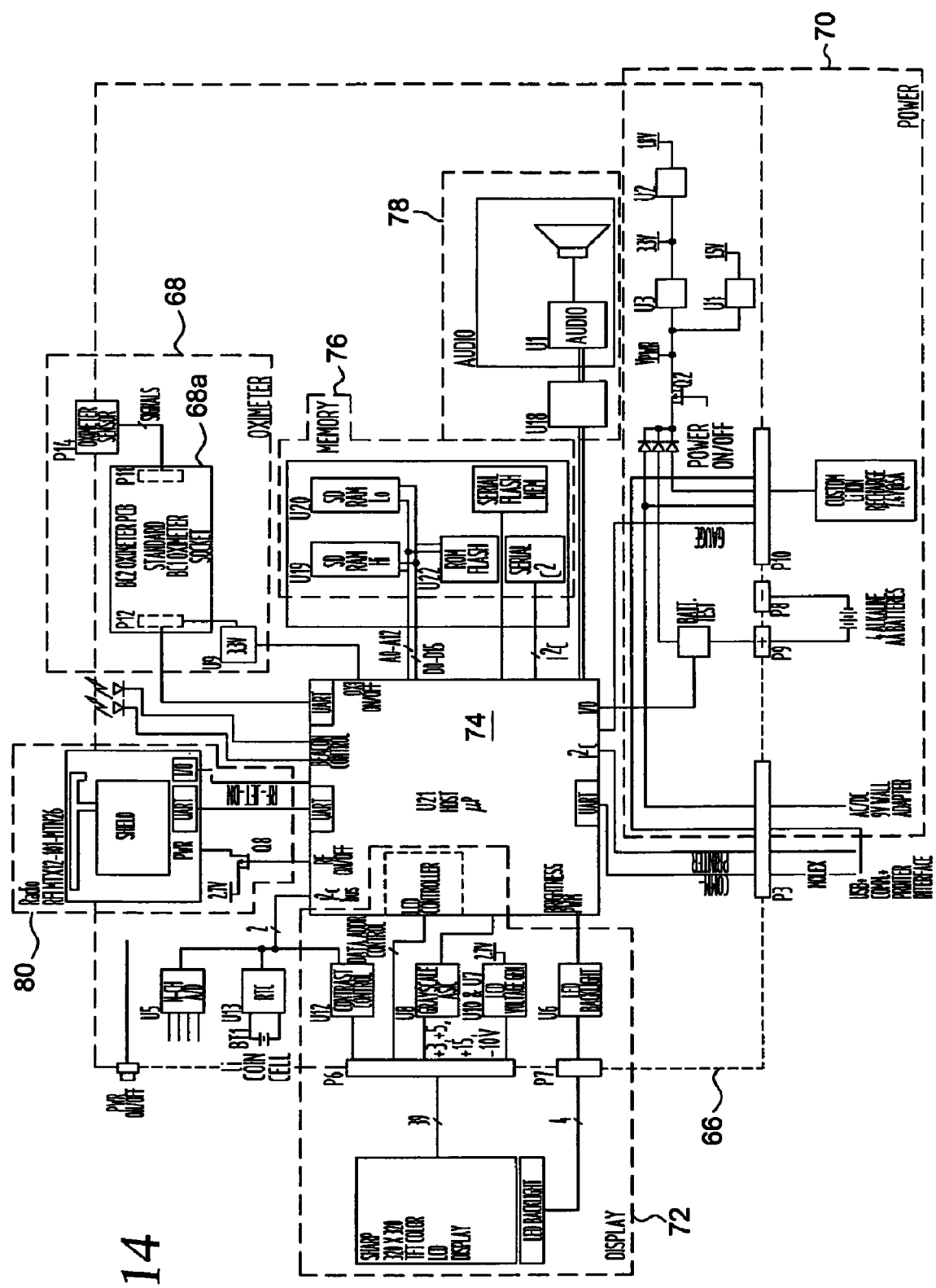
FIG. 14 is an exemplar circuit schematic of the inventive communicator of FIG. 13.

FIG. 14 is an exemplar schematic diagram of the communicator of the instant invention. As shown, the main communicator printed circuit board or module 66 is divided into a number of major modules or circuits. These circuits include oximeter module 68, power module 70, display module 72, the main processor 74 and its associated circuits on the PC board it is mounted to, memory module 76, audio module 78 and radio module 80. There are also miscellaneous circuits that include for example the realtime clock, A/D converter, and external communications circuitries. A docking station and a printer (not shown) may also be included in the system.

Oximeter module 68 comprises an oximeter PCB (print circuit board) of the assignee, designated 68a, that has a manufacturer reference PN 31392B1, or variants of PN 31402Bx or PN 31392Bx. This oximeter board communicates by way of a logic level, full duplex, Universal Asynchronous Receiver Transmitter (UART) from the P12 connector to the host processor 74. Power to the oximeter circuit board 68a is provided by power circuit 70 in the form of regulated 3.3 volt via connector P12 through switched capacitor regulator U9. Connector P11 at board 68 provides the connection to a connector P14 at main board 66, which is used to connect to a wired oximeter sensor. The signals received from the oximeter sensor are routed through board 68a, and by way of connector P12 to processor 74.

Power module 70 is adapted to be powered from multiple sources which include a universal mains AC/DC 9V wall mount power supply, a Universal Serial Bus (USB) powered at 5V at 500 mA, a user changeable AA (4 alkaline disposable batteries at 6V), and custom lithium ion rechargeable batteries at 7.4V. Whichever power is supplied is automatically arbitrated. The AC/DC 9V power and the USB 5V power enter through the general purpose docking/serial communications connector P3. The alkaline and lithium ion rechargeable batteries occupy the same internal battery compartment so that one or other can be present at any given time and each have their separate connections. The alkaline batteries are connected four in series by way of connectors P9 and P8, while the lithium rechargeable pack connects through the five-position connector P10. The lithium ion rechargeable pack contains integral charging control, fuel gauge, and redundant safety circuits. Additional signals on P10 are the AC/DC 9V power, USB 5V power plus 7.4V out, ground and 1-1 wire logical interface to the main processor 74 (U21) to communicate the charging and fuel gauge information. As shown, all of the possible power supplies are diode OR'ed to create a source that can range between 4.5V and 8.5V before being routed to the main on/off power MOSFET transistor Q2. The power source is then efficiently converted to 2.7V by way of a step down converter/switchable regulator U3. Other supply voltages of 1.8V and 1.5V are also created by regulators U2 and U1, respectively. The main processor U21 operates from the 2.7V, 1.8V and 1.5V supplies. The flash and SDRAM memories operate from the 1.5V supply. The radio and much of the general purpose I/O operate from the 2.7V supply.

The display circuit may comprise a color TFT 3.0 inch LCD display manufactured by the Sharp Electronics Company having a manufacturing number PN LQ030B7DD01. The display resolution is 320 H×320 V. Processor U21 provides an integral LCD controller peripheral that is capable of generating a majority of the required timing and LCD control signals. Four additional LCD related circuits (external to processor U21) are shown. Contrast control is provided through digital potentiometer (POT) U12 and commanded by the main processor U21 by way of an I$^2$C two-wire bus. AC and DC gray scale voltages are generated by the gray scale ASIC U8. Additional LCD supply voltages of +3V, +5V, +15V and −10V are generated by voltage regulators U7 and U10. The light emitting diode (LED) backlighting brightness is controlled by switching regulator U6. The brightness is controlled by the duty cycle of the pulse width modulator (PWM) control signal from main processor U21. The LCD display control signals are brought out from the display module by means of a 39-conductive flex flat cable which connects to the connector P6. The display back light LEDs are brought out from the module with a four conductive flex flat cable which connects to connector P7.

The main processor 71 (U21) may be an ARM-9 architecture processor from the Freescale Company with manufacturing number PN MC9328MX21VM. This processor has the many onboard peripherals that are needed including for example the LCD controller, multiple UART ports, I²C ports, external memory bus, memory management unit, multiple PWM outputs, low power shutdown modes, key scan and key debounce, to name a few of the components of the processor that are utilized in the communicator of the instant invention.

In the memory module 76, there are three different types of memories, two 8 Mb×16 SDRAM (Synchronous Dynamic RAM) at 1.8V as designated by U19 and U20, one 2 Mb×16 FLASH (non-volatile memory) at 1.8V designated by U22, and one 1 Mb serial EEPROM (Electrically Erasable PROM) at 2.7V. The program code and non-volatile trend data are stored in the Flash memory. At power-up the program code is transferred from the slower Flash memory to the higher speed SDRAM to support faster processor operation. The non-volatile serial EEPROM is used to store system event logs, system serial number, and other systems information. The non-volatile Serial Flash Memory is used for trend data storage. The display memory is executed out of the SDRAM memory space.

The audio module 78 supports audio alarms per the 60601-1-8 Alarm standard for medical devices. Due to the volume and tonal qualities dictated by the Alarm standard, a conventional voice coil speaker is used to generate the needed sounds, as opposed to using a piezoelectric type transducer. Main processor U21 generates a pulse width modulated (PWM) control signal with 11-bits of resolution to control both pitch and volume of the alarm signal. The signal conditioning circuitry U18 filters this PWM stream into an analog audio signal which in turn is amplified by a class D audio amplifier U15. U15 differentially drives an 8-ohm speaker in the conventional bridge tide load (BTL) configuration for maximum efficiency.

The radio circuit 80 has a radio module RF1 that may be a single board transceiver radio and PCB antenna designed to operate in accordance with the IEEE 802.15.4 Low Data Rate Wireless Personal Area Network (WPAN) standard. The radio module hardware is supplied by the L.S. Research company, located in Cedarburg, Wis., under the product name Matrix having a manufacturing number PN MTX12-101-MTN26. The matrix module is a 2.4 GHz 802.15.4 based module that is designed for proprietary and ZigBee (a low power, wireless networking standard) data transceiver applications. The processor and transmitter of the matrix module may be based on an integrated module such as for example the Texas Instrument CC2430 chip.

Figure 15:
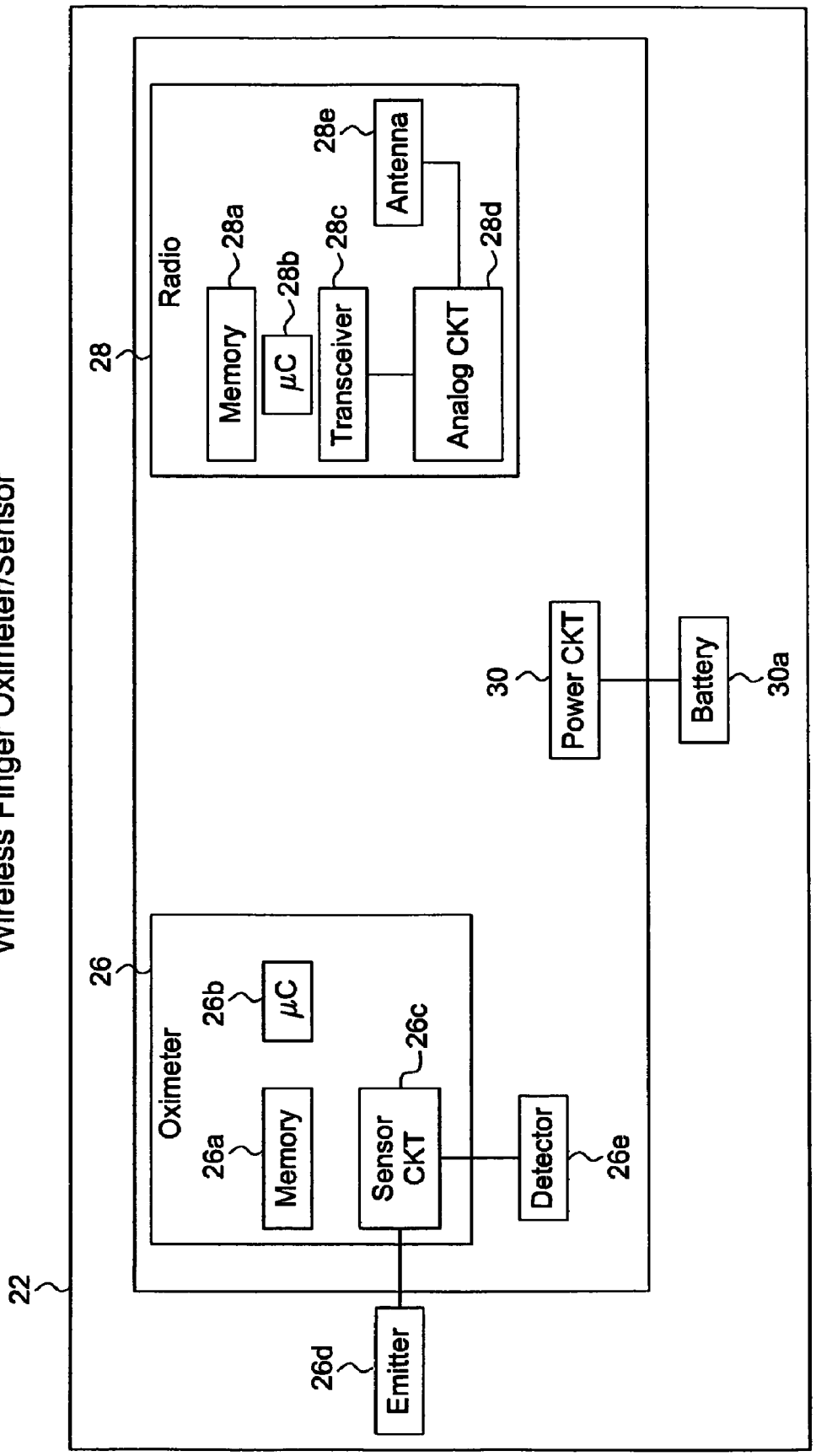
FIG. 15 is a diagram showing in more detail the various components of an exemplar wireless oximeter or sensor node of the instant invention.

With reference to FIG. 15, a more detailed exemplar wireless finger oximeter sensor corresponding to that in FIG. 5 is shown. Components that are the same as those in FIG. 5 are labeled the same here. The oximeter sensor 22 in FIG. 15 is shown to include an oximeter module 26 and a radio module 28. In the oximeter module 26 there is a memory 26a, a controller 26b and a sensor circuit 26c. The sensor circuit is connected to and provides the power to a light source emitter 26d as well as a detector 26e. The light emitter and the detector work in combination to detect or monitor the oxygen saturation in the blood of a patient connected to the emitter and detector. The data collected from the patient is stored in memory 26a. The overall operation of the oximeter module is controlled by controller 26b.

Radio module 28 has a memory 28a, a controller 28b, a transceiver 28c, an analog circuit 28d and an antenna 28e. The operation of the radio module 28 for the oximeter sensor device is similar to that discussed with respect to the communicator. However, in most instances, only data that is collected and stored in the oximeter module 26 is transmitted out by the radio transmitter. However, given that transceiver 28c is adapted to receive signals as well as to send out signals, radio module 28 of the oximeter sensor device 22 may be able to receive a signal from a remote source, for example a communicator, so as to receive instructions therefrom. One such instruction may be a sleep instruction sent by a communicator to instruct the oximeter to go into the sleep mode. Another possible instruction may be an awake instruction to wake the oximeter sensor from its sleep mode and to begin monitor the SP02 of the patient. As was discussed with respect to the timed functions illustrated in FIG. 12, the oximeter sensor device is adapted to receive a transmission from a communicator to which it is designated, so that it may be synchronized with the communicator, before data collected from the patient by the oximeter sensor is transmitted to the communicator.

Power is provided to the oximeter and radio modules of the oximeter sensor device 22 by power circuit 30, which regulates the power from a battery 30a. In most instances, the oximeter sensor device 22 is worn by the patient, with the sensor being specifically placed about a digit, such as for example the finger, of the patient. Other types of sensors such as for example reflective sensors that are attached to the forehead of a patient may also be used.

In operation, the processor controller 26b in oximeter module 26 controls an analog sensor circuit that samples the serially incoming analog waveform signal that corresponds to the being measured physical parameter of the patient. A program is processed by controller 26b to compute the digital oximetry data from the sampled analog waveform obtained from sensor circuit 26c. This digital data is then communicated to radio module 28, which transmits the data to the communicator that is within its transmission area, so that the data may be displayed by the communicator. Although the protocol utilized by radio module 28 is the same as that used by the radio module of the communicator, there may be hardware differences between the radio module in the oximeter sensor device and the radio module in the communicator. This is due to for example the omission of the power amplifier and the strengthening of the antenna because of the size versus performance tradeoffs that are necessary for the oximeter sensor device.

Figure 16:
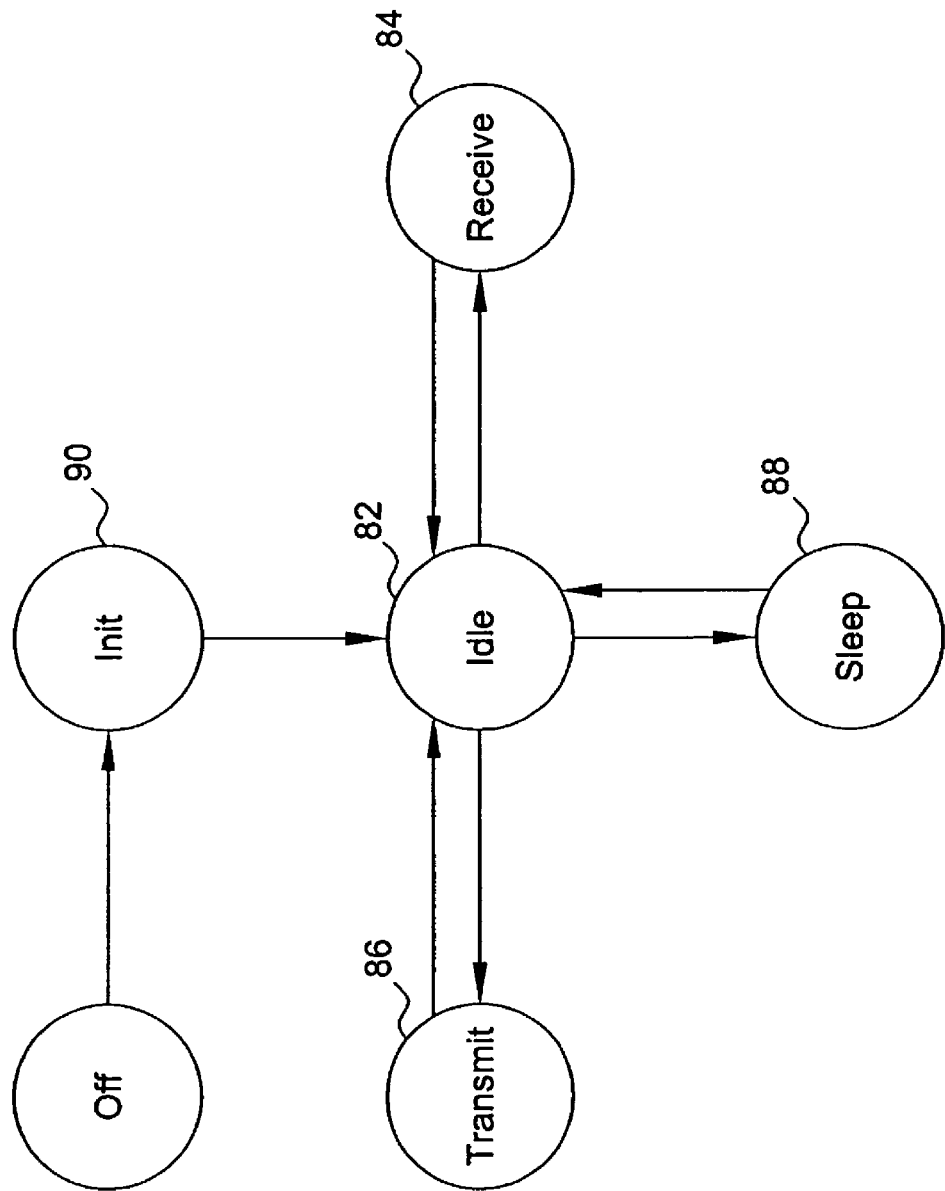
FIG. 16 is an illustration of the major states of the radio transmitter that may be used in the wireless oximeter sensor of the instant invention.

The major transition states of the radio module, based on RF interrupts—such as for example start, receive and micro controller control—is shown in FIG. 16. As shown, there are four primary states or modes. These are: idle state 82, receive state 84, transmit state 86, and sleep state 88. There is also an initialization state 90 required for the proper operation of the radio after a hard reset. In the idle state 82, the radio listens and upon detection of a proper RF signal, it begins to receive the incoming data. Upon command, the radio enters into the transmit state 86 where a buffered data packet is communicated over the RF interface out to the broadcast range of the radio. The sleep mode 88 allows the radio to operate at low power without losing its settings. The radio can be turned off in any state.

FIGS. 17-21 are flow charts illustrating the operation of the communicator of the instant invention.

Figure 17:
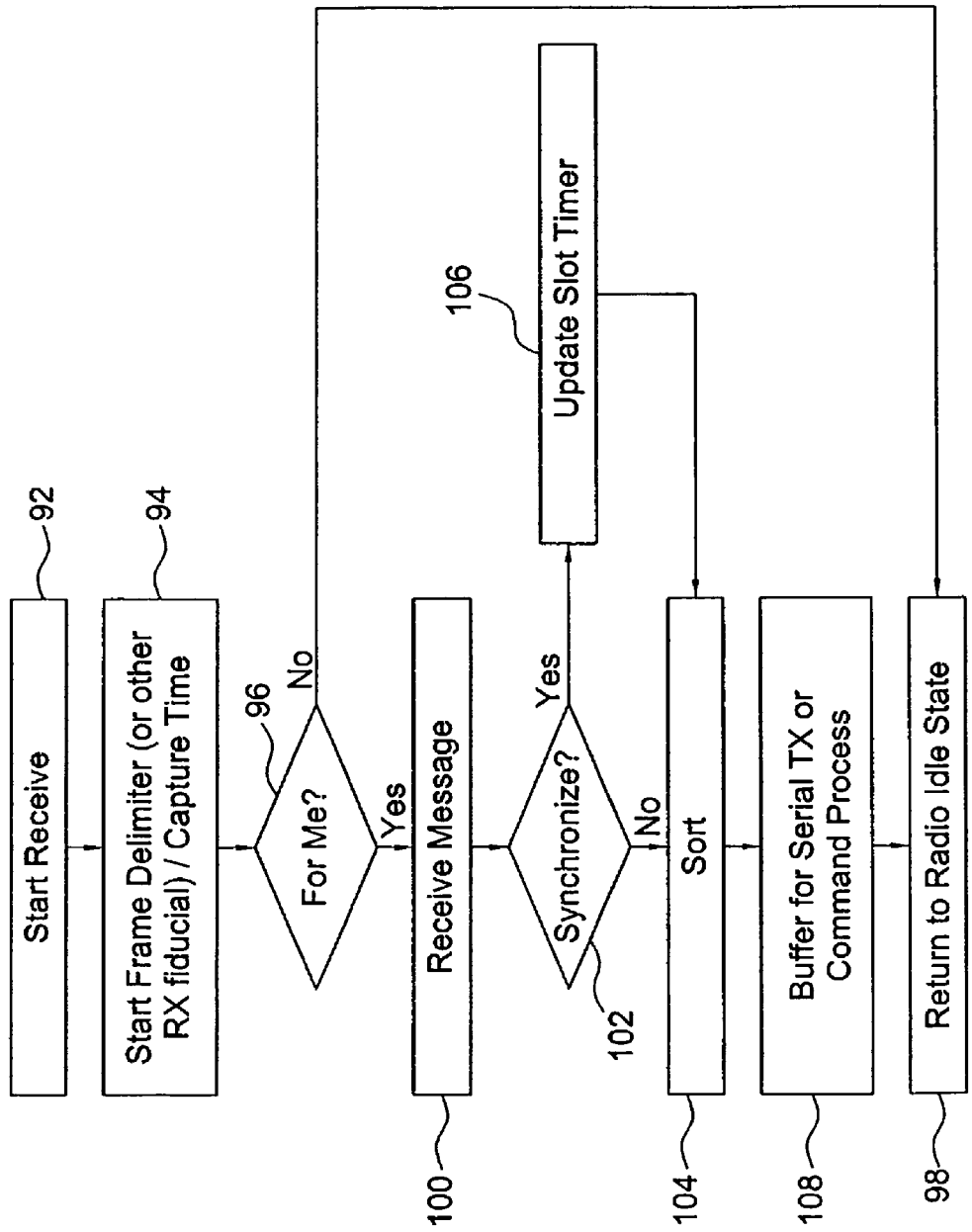
FIG. 17 is a flow diagram illustrating the operational steps the inventive communicator processes to receive information.

In FIG. 17, the radio module enters into the receive mode in step 92. This receive step follows the radio protocol and any additional software control. Upon detecting a fiducial signal, the controller of the radio records its current time, per step 94. Note that the fiducial signal is defined in the IEEE 802.15.4 standard as the start frame delimiter detection signal, and should have a relatively consistent time behavior. In step 96, a determination is made to verify whether the received packet is intended for the particular device, i.e., whether there is proper designation address and format. If the message is not intended for this particular radio, then the process returns to an idle state, per step 98. At that time, the message deemed not to be intended for the radio causes the radio to stop receiving data and to discard the data it has already received, before returning to the idle state. If the determination made in step 96 verifies that the message indeed is intended for the radio, then the process proceeds to step 100 where the message is received and buffered into the local memory of the radio. In step 102, a determination is made on whether the received message is to be used for synchronization. If it is not, the process proceeds to step 104 where the message is sorted. But if the message indeed is meant for synchronization, then the process proceeds to step 106 where the slot timer is updated based on the time of the fiducial signal, before the message gets sorted in step 104. Thereafter, the message is buffered appropriately in step 108 so that it may be serially transmitted to the host of the radio. Thereafter, the radio returns to its idle state per step 98.

Figure 18:
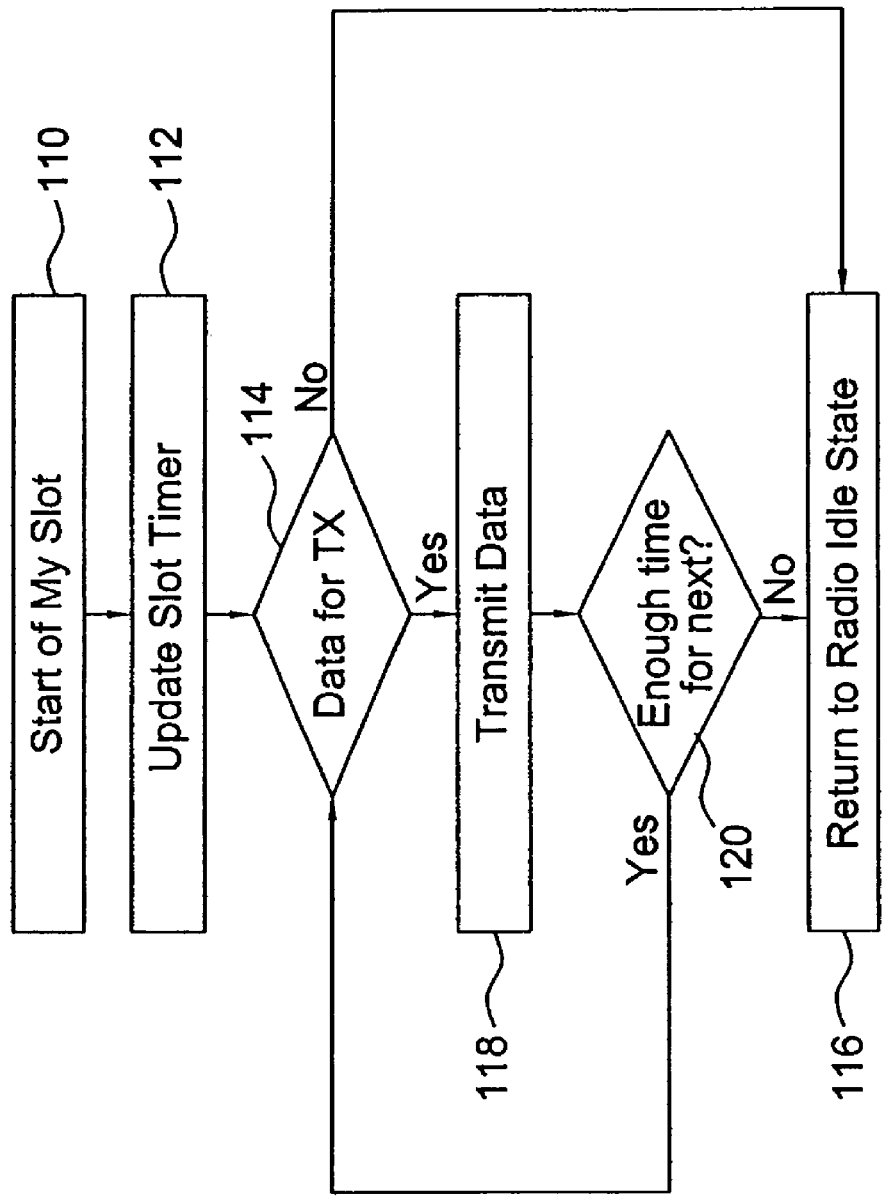
FIG. 18 is a flow chart that illustrates the process undertaken by the radio transmitter in the communicator, and also in the wireless sensor, to transmit data.

FIG. 18 is a flowchart illustrating the transmit process of the radio of the communicator. The radio starts transmitting upon command from the radio micro-controller. This is step 110. In this step, the micro-controller will signal the start of its time slot based upon the scheduling and the synchronized timing. Upon the start of a slot, the radio may update its slot timer, per step 112. This may be important if there is a single node in the network, (i.e., the communicator is not in the transceiving range of other communicators but is within the broadcast range of the wireless oximeter sensor), and the initialization protocol requires for regular broadcasting of messages. In step 114, a determination is made on whether there is data to be transmitted for a given time slot. If there is not, the process returns to the radio idle state, per step 116. If there is, the data is transmitted per step 118. In step 120, a determination is made on whether the time slot is long enough for another transmission. If it is, the process returns to step 114 to retrieve additional data for transmission. The process continues so long as there is enough time for transmitting more messages. If it is determined that there is no longer enough time for a next transmission in step 120, the process returns the radio to its idle state, per step 116, where the radio awaits the next transmit, receive or sleep instruction.

The aggregate and broadcast processes for the communicators are illustrated in the flow charts of FIGS. 19 and 20, respectively. In FIG. 19, the host processor of the communicator receives the RDD message, or other aggregate and forward type messages, from the radio, per step 122. The received data is then compared with the previously stored, or local copy of the message stored in the memory of the radio, per step 124. In step 126, a determination is made on whether the receive data is newer than the previously stored data. If it is, the local memory is updated with the received RDD message per step 128. The display on the communicator may be updated per step 130. The process then stops per step 132 until there is a next start. If in step 126 it is determined that the data received is not newer than the previously stated data, the aggregate process exits to step 132 to await the next incoming RDD message.

FIG. 20 is a flow chart illustrating the forward process for the communicator of the instant invention. Per step 134, the RDD table (which also includes the HS data and similar aggregate and forward messages) is updated with the local pulse oximetry data. In step 136, any new local pulse oximetry data is retrieved and readied. In step 138, the RDD message is updated. The process then exits per step 140.

Figure 21:
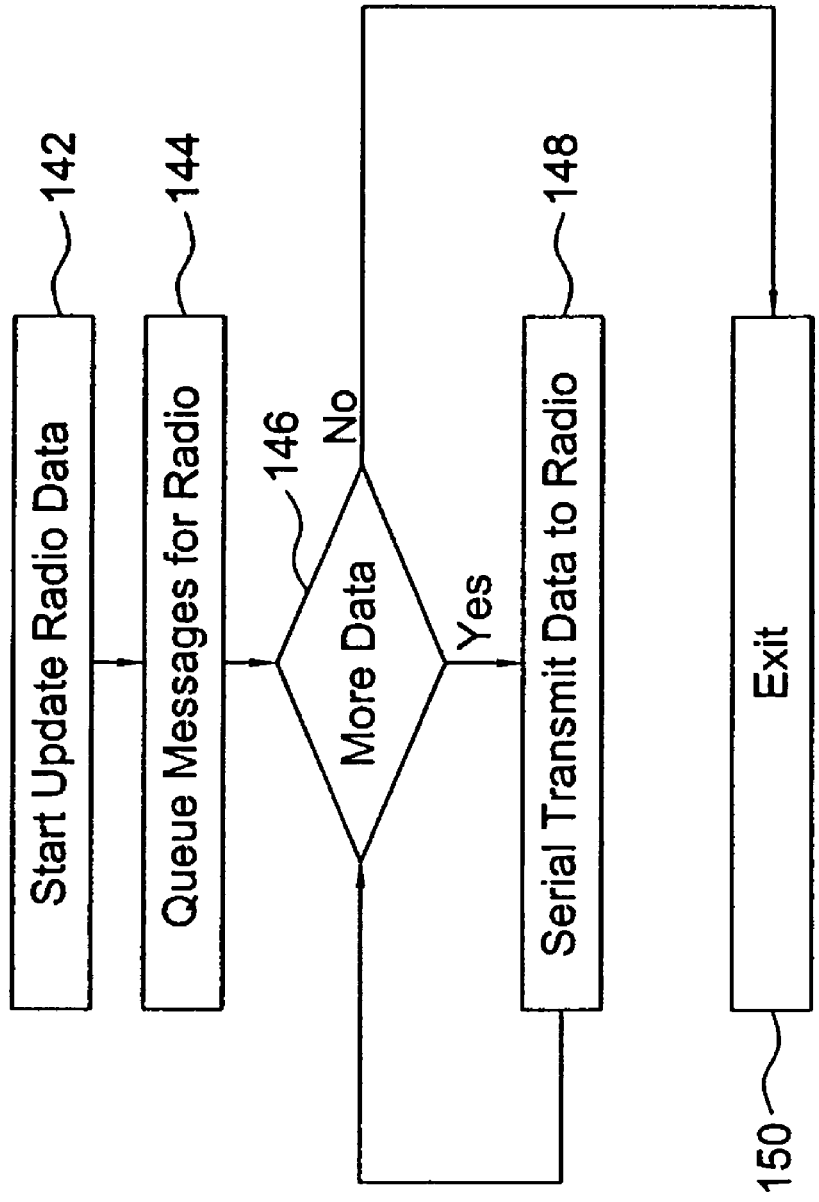
FIG. 21 is a flow chart illustrating the process of a communicator broadcasting the message that has been updated in its memory.

In FIG. 21, the processing steps for aggregating and forwarding the data to the radio module from the main processor of the communicator is illustrated. Starting at step 142, the data for the radio module is updated. Thereafter, in step 144, the messages are queued for the radio module. A decision is made on whether there is additional data in step 146. If there is, the additional data is serially transmitted to the radio module per step 148. The process continues until a determination is made, per step 146, that there is no more data to be routed to the radio. At which time, the process is routed to step 150 and the aggregating and forwarding process ends.

Figure 22:
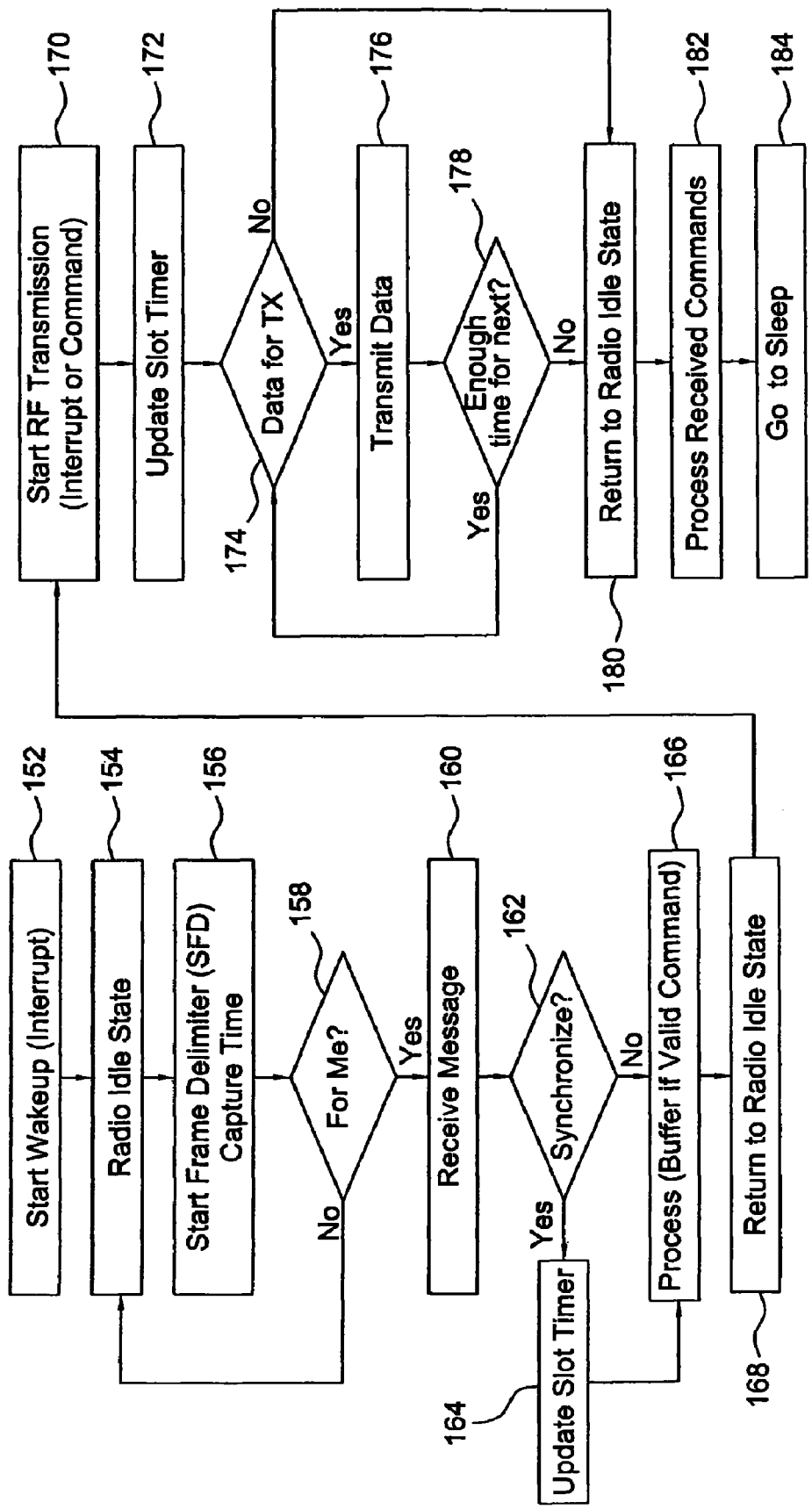
FIG. 22 is a flow diagram illustrating the operational processing steps of a wireless oximeter, or a sensor node, of the instant invention.

FIG. 22 is a flow chart that illustrates the operations of the wireless oximeter. So that power is conserved, as was noted above, the wireless oximeter sensor begins in a radio sleep mode. The process therefore begins at step 152 where the oximeter is awaken by either an external signal or an internal timer interrupt, as was discussed previously. The radio of the oximeter then goes into an idle state per step 154. From the idle state, the radio may receive data, be synchronized and returns to the idle state. These processes start with step 156 where the start frame delimiter (SFD) is reviewed to capture the time, per discussion with reference to FIGS. 11 and 12. If it is determined that the SFD is not for the oximeter in step 158, then the process returns to the idle state in step 154 to await the SFD that designates or identifies the oximeter sensor as the one. If the oximeter determines that it is the correct sensor to be communicating with the communicator, the process proceeds to step 160 where it receives the message. If the message is determined to be the synchronization message, per step 162, then the slot timer is updated per step 164 to synchronize the oximeter with the communicator. The process then proceeds to step 166 where the messages oncoming are buffered. The same buffering process also takes place if the message is determined not to be a synchronization message. Thereafter, the process returns to the radio idle state, per step 168.

The oximeter remains in the idle state until a start RF transmission interrupt or command is received per step 170. At that time, the slot timer is updated per step 172. In step 174, the process determines whether there is data for transmission. If there is, the data is transmitted per step 176. A determination is next made, per step 178, on whether there is enough time for transmitting the next message. If there is, the process returns to the step 174 to retrieve the next message, and transmits the retrieved message per step 176. The process repeats until it is determined, per step 178, that there is no longer enough time for the next message. At which time the process returns to the idle state per step 180. The process also goes into the idle state if it was determined in step 174 that there was no data for transmission. After the idle state, the process may receive further commands per step 182. Thereafter, as the radio and oximeter are independently powered, to conserve power, the radio is put to sleep per step 184 until it is awakened.

It should be appreciated that the present invention is subject to many variations, modifications and changes in detail. For example, even though the disclosed network, system and devices have been discussed with reference to a medical instrumentation environment, it should be appreciated that such network, system and devices are equally adaptable to operate in a non-medical setting. Thus, it is the intension of the inventors that all matter described throughout this specification and shown in the accompanying drawings be interpreted as illustrative only and not in a limiting sense. Accordingly, it is intended that the invention be limited only by the spirit and scope of the hereto appended claims.

The invention claimed is:

1. A system for communicating information relating to physical attributes of patients, comprising:
   at least one patient monitoring device associated with a patient having a sensor for detecting at least one physical attribute from the patient and at least a transmitter for transmitting patient data corresponding to the detected physical attribute out to a device transmission area; and
   a plurality of mobile communicators adapted to be positioned at different locations, each of said communicators having a transceiver for at least receiving data transmitted from said patient monitoring device when located within said device transmission area and to communicate with other communicators within a communicator transceiving area;
   wherein one of said communicators, when located within said device transmission area, receives the patient data from said patient monitoring device, and wherein after receipt of the patient data from said patient monitoring device, said one communicator broadcasts the patient data to other communicators that are located within its communicator transceiving area;
   wherein each of said plurality of communicators includes a memory for storing patient data of the patient, said each communicator receiving the patient data broadcast by said one communicator when moved to within the transceiving area of said one communicator, and wherein if there is patient data of the patient previously stored in the memory and if the received patient data is more recent than the stored patient data, the memory is updated with the received patient data so that the patient data stored in the memory of said each communicator is the most recent patient data.

2. The system of claim 1, wherein each of other of said plurality of communicators within the communicator transceiving area of said one communicator, upon receiving the patient data from said one communicator, updates patient data of the patient, if any, previously stored in said each other communicator with the received patient data, and broadcasts the updated patient data for dissemination to other communicators located within the communicator transceiving area of said each other communicator.

3. The system of claim 1, wherein there are at least two communicators located within said device transmission area, first of said two communicators broadcasting the patient data it received from said patient monitoring device in accordance to an assigned time slot time synchronized with another time slot assigned to second of said two communicators so that there is no interference in the transmission and reception of signals between the two communicators.

4. The system of claim 1, wherein said each communicator in receipt of the patient data aggregates the received patient data with data, if any, previously stored in its data store and thereafter broadcasts the aggregated patient data to its transceiving area.

5. The system of claim 1, wherein a remote communicator that is located out of the range of the device transmission area of said patient monitoring device is capable of receiving patient data of the patient so long as said remote communicator is within the transceiving area of said one communicator or is telecommunicatively linked to said one communicator indirectly via at least an other communicator so that a telecommunications path is established between said one communicator and said remote communicator.

6. The system of claim 1, wherein said patient monitoring device comprises an oximeter having a transceiver including said transmitter, said patient monitoring device wearable by the patient.

7. The system of claim 1, wherein each of said communicators comprises an oximeter having a radio transceiver adapted to both receive and transmit signals within its transceiving area, said each communicator including at least one memory for storing the patient data.

8. The system of claim 1, wherein there are multiple patient monitoring devices each associated with a particular patient, each of said multiple patient monitoring devices having a sensor means for detecting at least one physical attribute from its associated patient and at least a transceiver to at least transmit patient data corresponding to the detected physical attribute of the particular patient within a device transmission area; and
   wherein each of said plurality of communicators, when located within the device transmission area of said each patient monitoring device, receives the patient data transmitted from said each patient monitoring device in accordance to an assigned time slot time synchronized with respective time slots assigned to said multiple patient monitoring devices and others of said plurality of communicators so that there is no interference in the transmission and reception of data and/or signals among the multiple patient monitoring devices and the plurality of communicators.

9. The system of claim 1, wherein said patient monitoring device and each of said plurality of communicators are time synchronized with respect to a communications schedule for the transmission, reception and/or broadcasting of signals and/or data.

10. The system of claim 1, wherein said transmitter comprises an other of said communicators, and wherein said other communicator is located fixedly relative to said sensor so that a communications path is established between said other communicator and said one communicator.

11. A system for communicating information relating to physical attributes of patients, comprising:
    multiple patient monitoring devices each associated with a particular patient, each of the multiple patient monitoring devices having a sensor for detecting at least one physical attribute from the patient associated therewith and at least one transmitter for transmitting patient data corresponding to the physical attribute detected for the particular patient out to a transmission area of said each patient monitoring device; and
    a plurality of mobile communicators adapted to be positioned at different locations, each of said communicators having a transceiver adapted to receive patient data transmitted from patient monitoring devices when located within respective transmission areas of the patient monitoring devices, and to communicate with other communicators within its transceiving area;
    wherein each of said communicators, when located within the transmission area of any one of said patient monitoring devices, receives the patient data from said any one patient monitoring device and broadcasts the received patient data out to its communicator transceiving area;

wherein said each communicator includes a memory for storing patient data of the patients, said each communicator storing the received patient data in its memory, and wherein if there is patient data of a particular patient previously stored in the memory and if the received patient data of the particular patient is more recent than the stored patient data of the particular patient, the previously stored patient data is updated with the received patient data so that the patient data for the particular patient stored in the memory of said each communicator is the most recent patient data for the particular patient.

12. The system of claim 11, wherein other communicators located within the communicator transceiving area of said each communicator, when in receipt of the patient data broadcasted by said each communicator, thereafter broadcast the received patient data out to their respective transceiving areas.

13. The system of claim 11, wherein a remote communicator that is located out of the range of the device transmission area of any one of said patient monitoring devices receives the patient data of the patient associated with said any one patient monitoring device so long as said remote communicator is within the transceiving area of a given communicator located within the device transmission area of said any one patient monitoring device and is in receipt of the patient data from said any one patient monitoring device, or is telecommunicatively linked to said given communicator indirectly via at least an other communicator so that a telecommunications path is established between said given communicator and said remote communicator.

14. The system of claim 11, wherein said each communicator aggregates the received patient data with patient data, if any, previously stored in its data store and, provided that the received patient data is more up to date than the previously stored patient data, thereafter broadcasts the aggregated patient data to its transceiving area.

15. The system of claim 11, wherein said each communicator in receipt of patient data of a particular patient associated with a particular one of said multiple patient monitoring devices aggregates the received patient data with data, if any, previously stored in its data store and thereafter broadcasts the aggregated patient data of said particular patient to its transceiving area so that the aggregated patient data may be propagated further along by being broadcast by any other communicator located within the range of the transceiving area of said each communicator.

16. The system of claim 11, wherein each of said plurality of communicators, when located within the device transmission area of any one of said multiple patient monitoring devices, receives the patient data transmitted from said any one patient monitoring device in accordance to an assigned time slot time synchronized with respective time slots assigned to said multiple patient monitoring devices and others of said plurality of communicators so that there is no interference in the transmission and reception of signals among the multiple patient monitoring devices and the plurality of communicators.

17. The system of claim 11, wherein each of said multiple patient monitoring devices and each of said plurality of communicators are time synchronized with respect to a communications schedule for the transmission, reception and/or broadcasting of signals and/or data.

18. The system of claim 11, wherein the transmitter associated with at least one of said multiple patient monitoring devices comprises an other communicator located fixedly relative to the sensor of said at least one patient monitoring device adapted to communicate with said each communicator of said plurality of communicators.

19. The system of claim 11, wherein at least one of said plurality of communicator is movable to different locations relative to at least one other of said communicators and/or at least one of said multiple patient monitoring devices.

20. A system for disseminating information relating to physical attributes of patients remotely, comprising:
at least one oximeter associated with a patient having a sensor for detecting at least SP02 of the patient, said oximeter including a transceiver to at least transmit patient data corresponding to the detected SP02 away from said device;
a plurality of mobile communicators adapted to be positioned at different locations, each of said communicators having a transceiver for receiving data transmitted from said patient oximeter when located within the transmission range of said patient oximeter, said each communicator further can communicate with other communicators;
wherein one of said communicators, when located within the transmission range of said patient oximeter, receives the patient data from said patient oximeter, said one communicator including a memory for storing patient data of the patient, and wherein if there is patient data of the patient previously stored in the memory and if the received patient data is more recent than the stored patient data, the memory is updated with the received patient data, said one communicator thereafter broadcasting the received patient data to other communicators that are located within its transmission range.

21. The system of claim 20, wherein each of said communicators comprises an oximeter having means to display at least the received patient data, and a memory for storing patient data, wherein the patient data of the patient stored in the memory is updated when new patient data of the patient is received for said each communicator.

22. The system of claim 20, further comprising:
another communicator located out of the transmission range of said patient oximeter but nonetheless receives the patient data when it is within the broadcast range of said one communicator so that it is able to receive the patient data broadcast by said one communicator, said communicator movable relative to said patient oximeter.

23. The system of claim 20, wherein said patient oximeter and the plurality of communicators each are assigned a given time slot synchronized with other time slots to effect time scheduled communications among said patient oximeter and the plurality of communicators.

* * * * *